(12) United States Patent
Keady et al.

(10) Patent No.: US 9,757,069 B2
(45) Date of Patent: Sep. 12, 2017

(54) SPL DOSE DATA LOGGER SYSTEM

(75) Inventors: John Keady, Boca Raton, FL (US);
Steven Goldstein, Delray Beach, FL (US); Gary Hoshizaki, Boynion Beach, FL (US); Marc Boillot, Plantation, FL (US); John Usher, Montreal (CA)

(73) Assignee: Staton Techiya, LLC, Delray Beach, FL (US)

( * ) Notice: Subject to any disclaimer, the term of this patent is extended or adjusted under 35 U.S.C. 154(b) by 1238 days.

(21) Appl. No.: 12/352,323

(22) Filed: Jan. 12, 2009

(65) Prior Publication Data
US 2010/0135502 A1   Jun. 3, 2010

Related U.S. Application Data

(60) Provisional application No. 61/020,400, filed on Jan. 11, 2008.

(51) Int. Cl.
| | |
|---|---|
| *H04R 29/00* | (2006.01) |
| *A61B 5/00* | (2006.01) |
| *A61B 5/12* | (2006.01) |
| *G01H 3/14* | (2006.01) |

(52) U.S. Cl.
CPC .......... *A61B 5/6817* (2013.01); *A61B 5/121* (2013.01); *G01H 3/14* (2013.01); *H04R 29/00* (2013.01)

(58) Field of Classification Search
CPC ........ A61B 5/121; A61B 5/6817; G01H 3/14; H04R 29/00; H04R 29/001; H04R 29/004; H04R 27/00; H04S 7/301

USPC ............... 381/56, 72, 380, 57; 73/646, 645; 181/129

See application file for complete search history.

(56) References Cited

U.S. PATENT DOCUMENTS

| | | | |
|---|---|---|---|
| 3,697,973 A | 10/1972 | Stevens et al. | |
| 3,802,535 A * | 4/1974 | Peake et al. | 73/646 |
| 3,848,471 A | 11/1974 | Hamburg et al. | |
| 3,968,334 A | 7/1976 | Padilla | |
| 4,020,298 A | 4/1977 | Epley et al. | |
| 4,060,701 A | 11/1977 | Epley | |
| 4,307,385 A | 12/1981 | Evans et al. | |
| 4,955,070 A * | 9/1990 | Welsh et al. | 455/2.01 |
| 5,317,273 A | 5/1994 | Hanson et al. | |
| 5,430,826 A | 7/1995 | Webster et al. | |
| 5,577,511 A * | 11/1996 | Killion | 600/559 |
| 5,757,930 A | 5/1998 | Seidemann et al. | |
| 6,456,199 B1 | 9/2002 | Michael | |

(Continued)

FOREIGN PATENT DOCUMENTS

GB   2323295 A * 9/1998

*Primary Examiner* — Vivian Chin
*Assistant Examiner* — Con P Tran

(57) ABSTRACT

A method for using an earpiece (800) in a work environment is provided. The earpiece (800) attenuates sound from the work environment to the user's ear. The earpiece (800) includes an ear canal microphone (820) for measuring a sound pressure level in an ear canal of the user. Sound pressure levels are measured periodically while in the work environment. Each measured sound pressure levels is stored in memory (127) of the earpiece with time and location information. The sound pressure level information is downloaded to a database (1704) when the earpiece is removed from the user ear for recharging. The sound pressure level information is analyzed and any potential noise compliance issues in the work environment are identified.

19 Claims, 18 Drawing Sheets

(56) References Cited

U.S. PATENT DOCUMENTS

| | | | | |
|---|---|---|---|---|
| 6,661,901 | B1* | 12/2003 | Svean et al. | 381/328 |
| 6,826,515 | B2* | 11/2004 | Bernardi et al. | 702/191 |
| 7,151,835 | B2* | 12/2006 | Yonovitz et al. | 381/56 |
| 7,227,968 | B2* | 6/2007 | van Halteren et al. | 381/328 |
| 7,308,105 | B2* | 12/2007 | Bullen | 381/57 |
| 7,450,730 | B2* | 11/2008 | Berg et al. | 381/312 |
| 7,983,426 | B2* | 7/2011 | Schuler et al. | 381/56 |
| 2004/0215053 | A1* | 10/2004 | Jorgensen et al. | 600/25 |
| 2005/0254665 | A1 | 11/2005 | Vaudrey et al. | |
| 2005/0254667 | A1 | 11/2005 | Michael | |
| 2007/0129828 | A1* | 6/2007 | Lee et al. | 700/94 |
| 2011/0054243 | A1* | 3/2011 | Davis et al. | 600/28 |

* cited by examiner

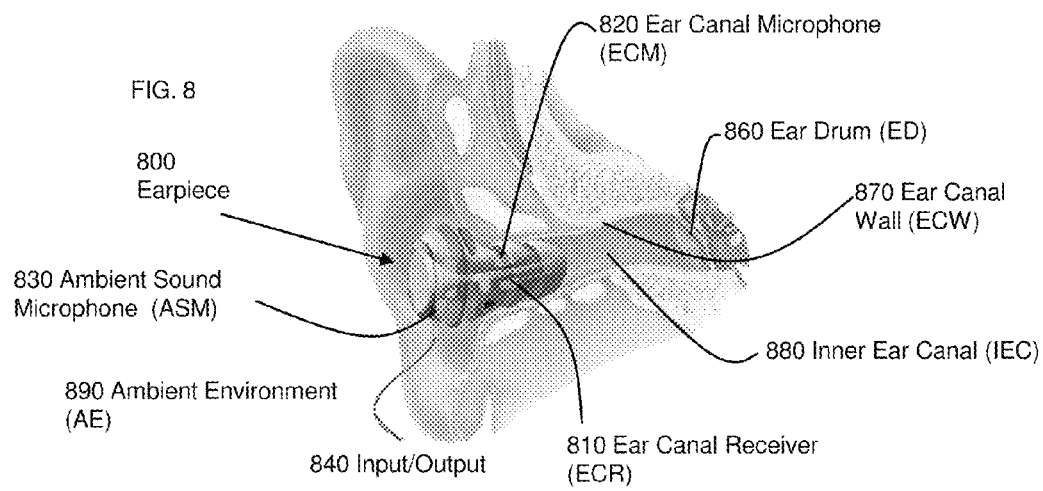
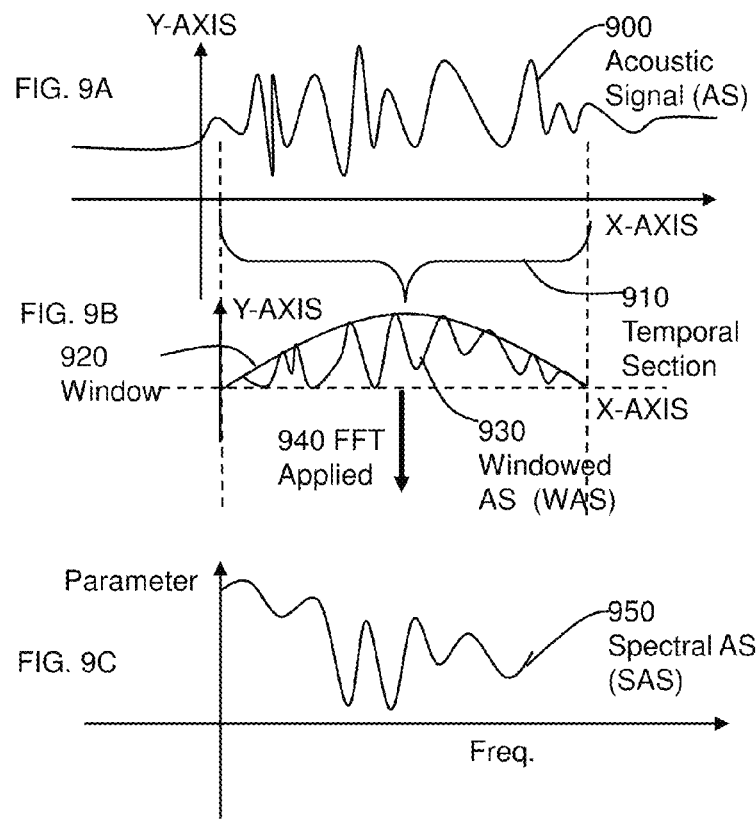

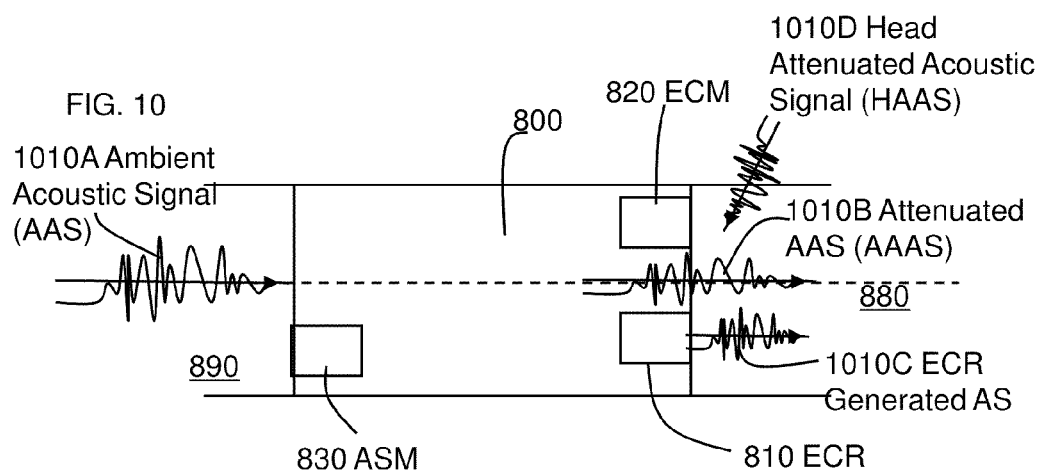
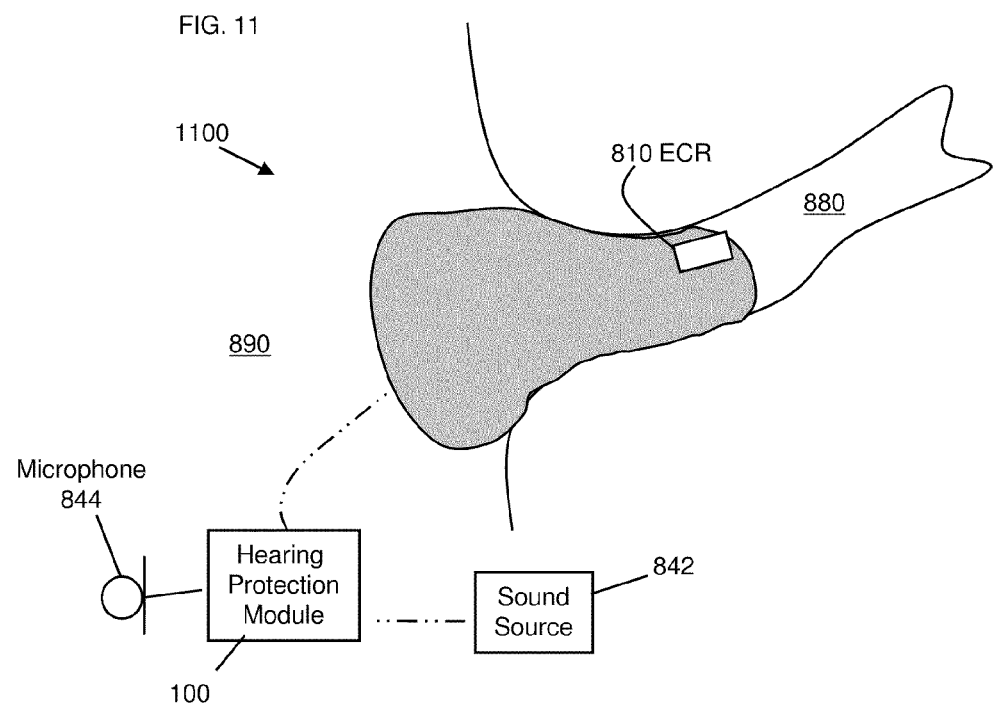

$(SPL_{ASM}, SPL_{ECM}, X,Y,Z,t)$

SPL map for a given workplace at a given time t, or averaged

SPL-Dose map for a given workplace at a given time t, or averaged

Note various doses can be displayed, e.g., the OSHA Noise Dose standards

FIG. 20
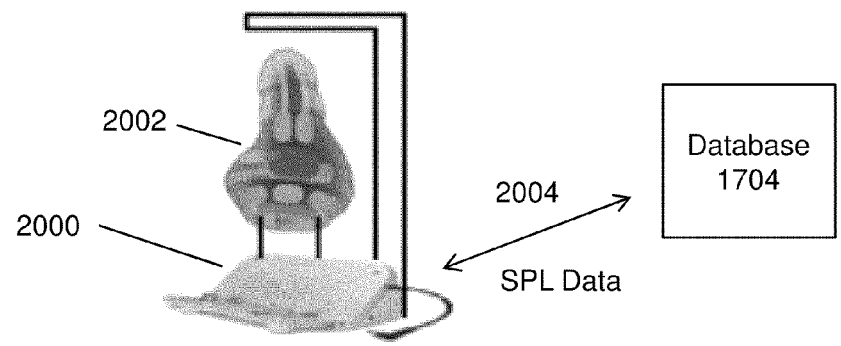
FIG. 21      2100
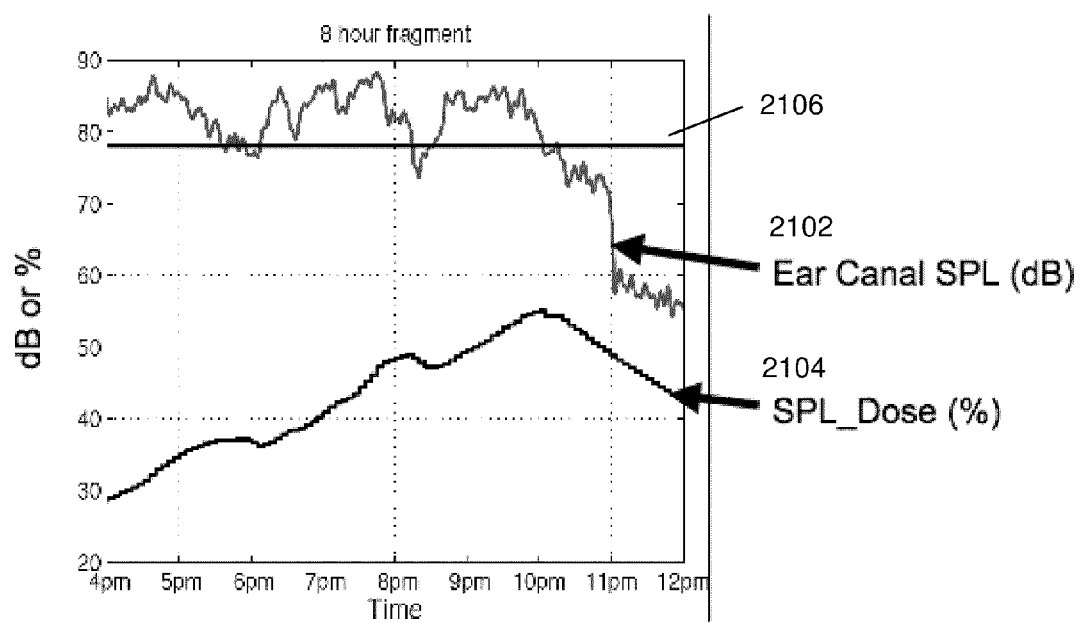

2200

| FS | Number of 8 bit Channels | | | | | |
|---|---|---|---|---|---|---|
| | 1 | 2 | 3 | 4 | 5 | 6 |
| 10 | 6912 | 13824 | 20736 | 27648 | 34560 | 41472 |
| 0.5 | | 691.2 | 1036.8 | 1382.4 | 1728 | 2073.6 |
| 0.1 | 69.12 | 138.24 | 207.36 | 276.48 | 345.6 | 414.72 |

US 9,757,069 B2

SPL DOSE DATA LOGGER SYSTEM

CROSS-REFERENCE TO RELATED APPLICATIONS

This Application is a Non-Provisional and claims the priority benefit of Provisional Application No. 61/020,400 filed on 11 Jan. 2008.

FIELD

The present invention relates to a device that monitors acoustic energy directed to an ear, and more particularly, though not exclusively, to an earpiece that monitors acoustic sound pressure level dose received by a user's ear.

BACKGROUND

With the advent of an industrial society, people are exposed to noise pollution at greater and greater levels from background noise such as street traffic, airplanes, and construction sites, as well as intentional high sound level exposure due to cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise.

It is also known from the related art that headphones for consumer electronics have been provided with a predetermined maximum output level in an attempt to prevent ear damage. This approach is ineffective as it does not take into account listening duration and the calculation of risk for auditory injury. Other headphones are maximum-limited to produce levels that can still result in significant overexposure given enough time, or limit the user to levels, which may not be sufficient to achieve an adequate short term listening level. In the latter case, consumer acceptance for the protective gear could be severely limited and a product would fail to survive in a competitive market and therefore be of no use.

Accordingly, a system that overcomes the shortcomings in the related art would be useful.

BRIEF SUMMARY

A method for monitoring sound pressure levels and mitigating hearing damage using an earpiece is provided. The earpiece attenuates sound from an ambient environment from reaching the ear canal of the user. The earpiece includes at least one transducer and stored in memory with time and location information. Sound pressure level information stored in the earpiece is downloaded to a database when the earpiece is coupled for recharging.

A method for using an earpiece in a work environment is provided. The earpiece attenuates sound from the work environment to the user's ear. The earpiece includes an ear canal microphone for measuring a sound pressure level in an ear canal of the user. Sound pressure levels are measured periodically while in the work environment. Each measured sound pressure levels is stored in memory of the earpiece with time and location information. The sound pressure level information is downloaded to a database when the earpiece is removed from the user's ear for recharging. The sound pressure level information is analyzed and any potential noise compliance issues in the work environment are identified.

A method of mapping sound pressure levels is provided using earpieces for attenuating sound in a work environment. Each earpiece has at least one transducer. The earpieces periodically measure sound pressure levels and SPL Dose. The SPL Dose is measured by an ear canal microphone. The measured sound pressure levels and SPL Doses are stored in a database. A map is generated of sound pressure level or SPL Dose for a predetermined area over a predetermined time or predetermined time period.

BRIEF DESCRIPTION OF THE DRAWINGS

FIG. 8 illustrates the general configuration and terminology in accordance with descriptions of exemplary embodiments;

FIGS. 9A-9C illustrate an example of a temporal acoustic signal and its conversion into a spectral acoustic signature;

FIG. 10 illustrates a generalized version of an earpiece and some associated parts in an ear canal;

FIG. 11 illustrates an earpiece according to at least one exemplary embodiment comprising an ECR;

FIG. 20 is a diagram of an earpiece battery charger in accordance with an exemplary embodiment;

FIG. 21 is a graph of a measurement of sound pressure level and SPL_Dose in accordance with an exemplary embodiment;

DETAILED DESCRIPTION OF THE INVENTION

Figure 1:
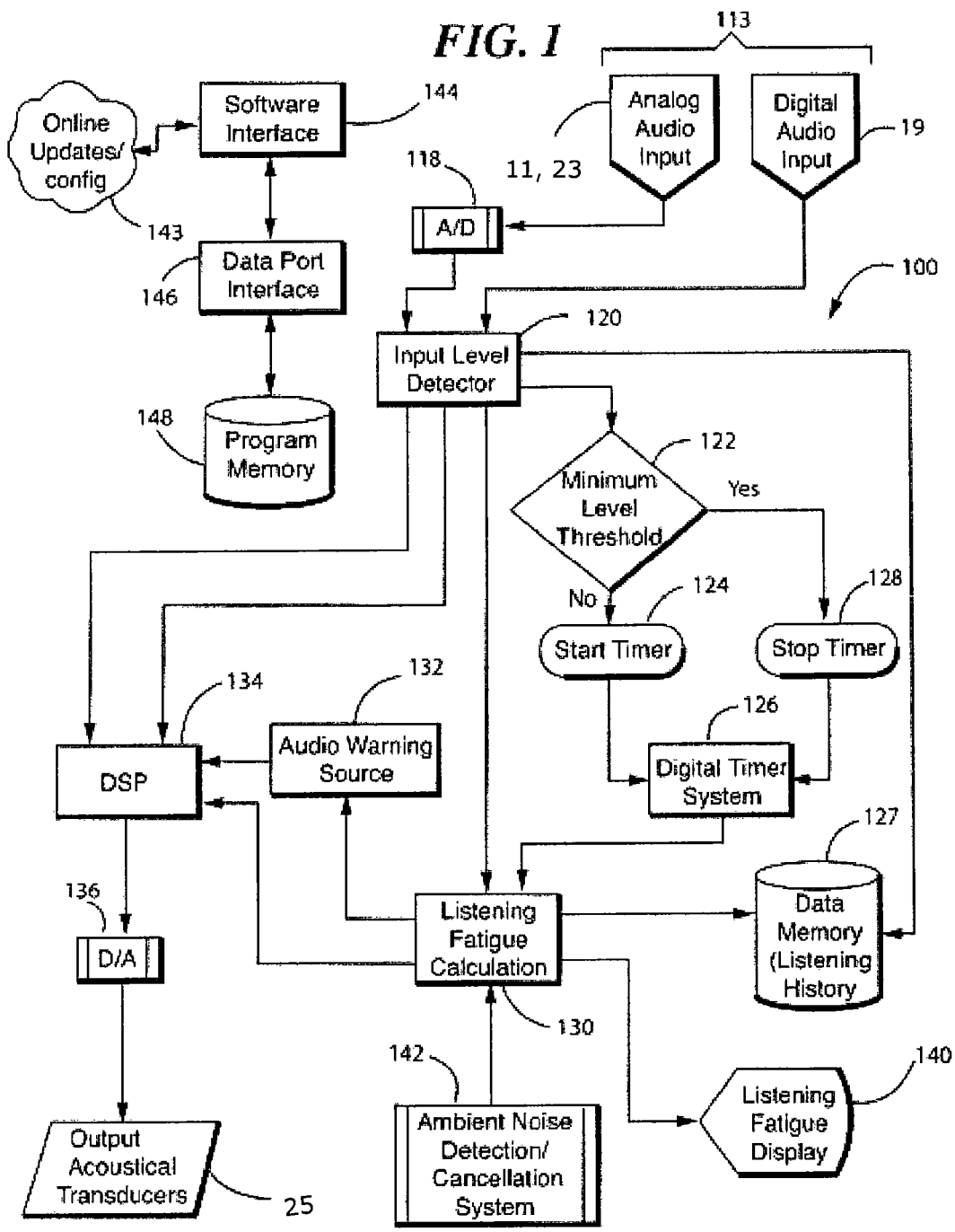
FIG. 1 is a block diagram of the system for measuring and determining exposure to sound over time at the ear in accordance with at least one exemplary embodiment of the invention.

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers. Additionally in at least one exemplary embodiment the sampling rate of the transducers can be varied to pick up pulses of sound, for example less than 50 milliseconds.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed in following figures.

Note that herein when referring to correcting or preventing an error or damage (e.g., hearing damage), a reduction of the damage or error and/or a correction of the damage or error are intended.

At least one exemplary embodiment of the invention is directed to measuring and determining the exposure of the ear to sound over time. Reference is made to FIG. 1 in which a system, generally indicated as 100, is constructed in accordance with at least one exemplary embodiment of the invention. System 100 includes an audio input device 113 for receiving sound at the ear. As will be discussed below, audio input device 113 can include an analog audio input 11, 23 and a digital audio input 19. In at least one exemplary embodiment, audio input device 113 receives audio input from at least one of three sources, namely; ambient noise around the ear, direct input noise such as a MP3 player or other device which can produce a digital audio input at digital audio input 19, and noise as detected or estimated within the ear canal 31 (FIG. 2B). The audio input device 113 outputs an audio signal corresponding to the received sound. Analog output signals from analog audio inputs 11, 23 are converted to a digital signal by an analog-to-digital (ND) converter 118 so that digital sound signals are input into an input level detector 120.

Input level detector 120 determines the sound pressure level of the sound received at audio input device 113. Input level detector 120 outputs a sound pressure level (SPL) signal, which is input to a minimum-level threshold detector 122. Minimum level threshold detector 122 determines whether or not the sound pressure level as detected by input level detector 120 exceeds a minimum level threshold. As will be discussed below, the minimum level threshold can be the permissible sound level PSL (e.g., effective quiet level) of the individual, or some predetermined level substantially corresponding to a level, which is ear damage neutral over time, or a level of interest, such as 80 dB, because of its effect on the ear. Therefore, if the minimum level threshold is detected as being exceeded, a signal indicating a sound pressure level in excess of the minimum level threshold is output to a start timer 124, which triggers a digital timer system 126 to begin a clock. Conversely, if the input sound pressure level is detected as being below the minimum threshold, a signal indicating the sound pressure level is below the minimum level threshold is output to a start timer 124, which triggers a digital timer system 126 to begin a clock of a restorative period. If the sound pressure level is at the minimum threshold (within a margin of error), no clock needs to be started because this is neutral to the desired effect. In a preferred embodiment, the clock signal is changed with every significant (more than 1 dB by way of example) change in sound pressure level to get an accurate profile of sound exposure over time.

Once the sound pressure level as detected at input level detector 120 decreases to or is below the minimum threshold level, a stop timer signal is output from stop timer 128 to digital timer system 126 to stop the clock corresponding to exposure to the excessively intense level. Digital timer system 126 outputs a clock value corresponding to the time period at which the minimum level threshold was not met, or in the preferred embodiment, for each period corresponding to a discrete level change.

A data memory or learning history database 127 receives the clock value from digital timer system 126 as well as the actual input level detected at input level detector 120 and determines a listening history or sound pressure level exposure history. The sound pressure level exposure history is a record of the user's exposure to sound pressure levels over time. Because the effect of exposure is cumulative, it is important that the exposure history be maintained. The listening history, as will be discussed below, can include real ear level data, listening duration data, time between listening sessions, absolute time, sound pressure level dose (SPL_Dose) data, including any restorative sound level, number of acoustic transients and crest factor and other data.

The sound pressure level exposure history or listening history includes both the listening habits history and the environmental or ambient noise exposure history. The environmental noise exposure history is the exposure of a user to environmental noise over time as a result of the auditory stimuli inherent to the environment where the user is present. This can be highway traffic, construction site, even the restorative effect of the quiet sound pressure levels, e.g., those typically encountered in a library whereas, the listening habits history is associated for the purposes for this disclosure with user-directed auditory stimuli such as music, words, other noises, which a user intentionally encounters for a purpose such as communication, learning, and enjoyment. Therefore, database 127, as will be discussed below, stores the cumulative SPL exposure.

It should be noted that in at least one exemplary embodiment, minimum level threshold detector 122 also starts the timer 124 when the sound pressure level is below the predetermined level. In this way, the restorative effect of sound levels below PSL (e.g., effective quiet noise) is accumulated for determining overall exposure damage potential.

In effect, the only time that digital timer system 126 is not running is when the detected sound pressure level signal is at the minimum level threshold. A listening fatigue calculator 130 receives the input level signal from input level detector 120 and data from the data memory listening history 127, and determines whether or not listening fatigue or hearing damage is likely to occur as a result of further exposure. Hearing damage is the injury to the hearing mechanism including conductive and sensorineural decrement in hearing threshold levels. It can be either temporary or permanent so long as it is a result of the noise exposure that is above PSL (e.g., Effective Quiet). In other words, listening fatigue calculator 130 will output a signal when a threshold sound exposure, determined as a function of exposure time and sound pressure level, as will be discussed in greater detail below, is achieved. At that point, a listening fatigue signal is output.

It should be noted that in an alternative embodiment, system 100 can make use of an ambient noise detection/cancellation system 142 as known in the art. These systems produce signals, which cancel sound pressure levels at certain frequencies and/or certain levels to reduce the effect of undesired noise, whether environmental noise or user directed noise. It will have some effect in elongating the permissible exposure time by negating the sound pressure level detected by input level detector 120.

In at least one exemplary embodiment, the signal from the listening fatigue calculator is utilized to prevent damage and encourages some action by the user when exposure levels are near damaging levels. Therefore, in one non-limiting example, a listening fatigue display 140 is provided for receiving the signal from the listening fatigue calculator and displaying to the user a prompt to discontinue exposure to the sound level from the damaging sound source or audio source.

In another non-limiting example, the signal from the listening fatigue calculator is output to an audio warning source 132, which outputs an output audio warning to the user notifying the user that exposure to the sound source has reached critical levels.

In at least one exemplary, but non-limiting, embodiment, system 100 is coupled to an earpiece and at least one sound source. The earpiece includes an output acoustical transducer 25 to provide an audio signal to the ear. In at least one exemplary embodiment, system 100 can modify audio content output by acoustical transducer 25. System 100 is wired or wirelessly connected in the signal path to acoustical transducer 25 for measuring and modifying the audio content provided to acoustical transducer 25. Digital signal processor (DSP) 134 receives a digital audio signal from input level detector 120, which acts as a pass through for the digitized signals from audio input device 113. Digital signal processor 134 passes the sound signals through to a digital to analog (D/A) converter 136 to drive acoustical transducer 25 to recreate the sound received at audio input device 113 inside the ear canal 31 in at least one exemplary embodiment of the invention as shown in FIG. 2B. With such an exemplary embodiment, audio warning source 132 provides an output to digital signal processor 134 causing output acoustical transducer 25 to output a warning sound inside the ear of the user.

Additionally, in at least one further exemplary embodiment, listening fatigue calculator 130 outputs a listening fatigue signal to digital processor 134 which causes digital signal processor 134 to attenuate the sound signal prior to output to acoustical transducer 25 to reduce the signal output level by any of the linear gain reduction, dynamic range reduction, a combination of both, or a complete shutdown of transducer 25. Attenuation would be at least to the level, if not below, the PSL (e.g., effective quiet level) to allow for ear recovery prior to damage.

It should be noted, that because personal hearing threshold and discomfort levels can change from person to person, and because both of the time intervals are a function of many variables, in a non-limiting example, to provide a dynamic ever-changing response, system 100 operates under software control. The configuration of the digital sound processor 134, listening fatigue calculator 130, the minimum level threshold detector 122, and the input level detector 120 are operated under software control.

In an exemplary embodiment of the invention, the control programs are stored in a program memory 148 for operating the firmware/hardware identified above. Furthermore, the program stored within memory 148 can be personalized as a result of testing of the user's ear, or by other modeling methods, in which system 100 includes a software interface 144 for receiving online or remote source updates and configurations. The software interface 144 communicates with a data port interface 146 within system 100, which allows the input of software updates to program memory 148. The updates can be transmitted across a distributed communications network, such as the Internet, where the updates take the form of online updates and configurations 143.

Also note that when referring to measurements in Decibels (dB) one is referring to a logarithmic ratio. For example dB is defined as:

$$SPL = \beta(dB) = 10\log\frac{I}{I_0} = 10\log\frac{\Delta P^2}{\Delta P_0^2} \qquad (1)$$

Where I is the intensity measured, $I_0$ is a reference intensity, $I_0=10^{-12}$ W/m$^2$, and $P_0$ is a reference pressure, $\Delta P_0=20$ micropascals, and where $\Delta P$ is the root mean squared pressure amplitude in a measured pressure wave (e.g., using a transducer). Thus, the sound pressure level (SPL) can be measured in dB.

Alternatively, one can use the above equation and solve for measured pressures instead. For example:

$$\Delta P(t) = 10^{(SPL(t)/20.0)}\Delta P_0 \qquad (2)$$

In the discussion of formulas herein we refer to SPL as a non-limiting example and one of ordinary skill in the arts could re-derive the equations in terms of measured pressures, ΔP, both are intended to lie within the scope of at least one exemplary embodiment.

Figure 2A:
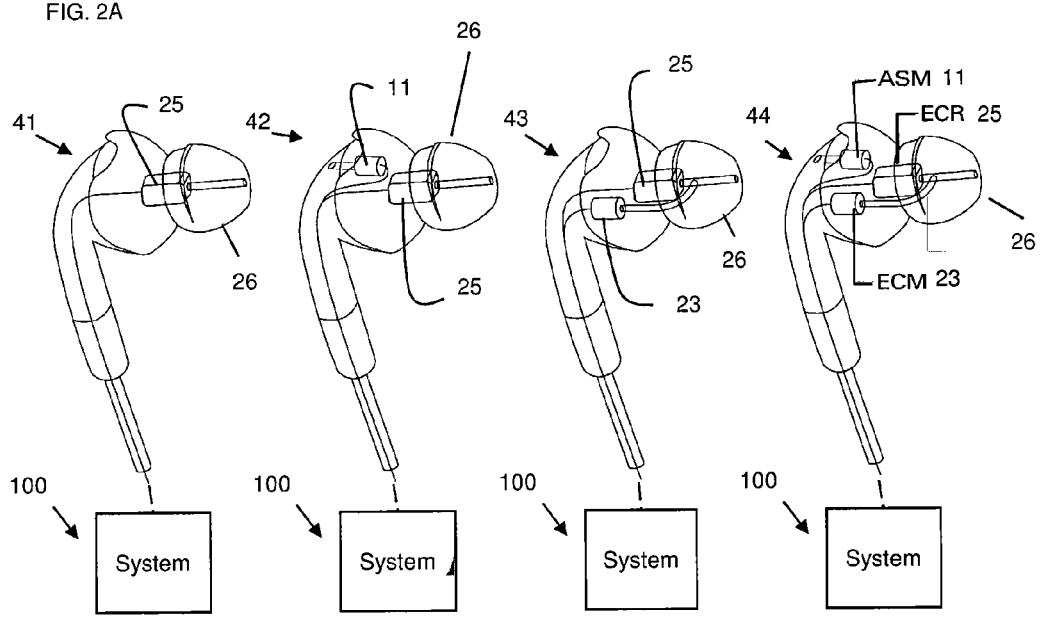
FIG. 2A illustrates various transducer configurations of an earpiece coupled or operatively connected to a hearing protection module of at least one exemplary embodiment.
Figure 2B:
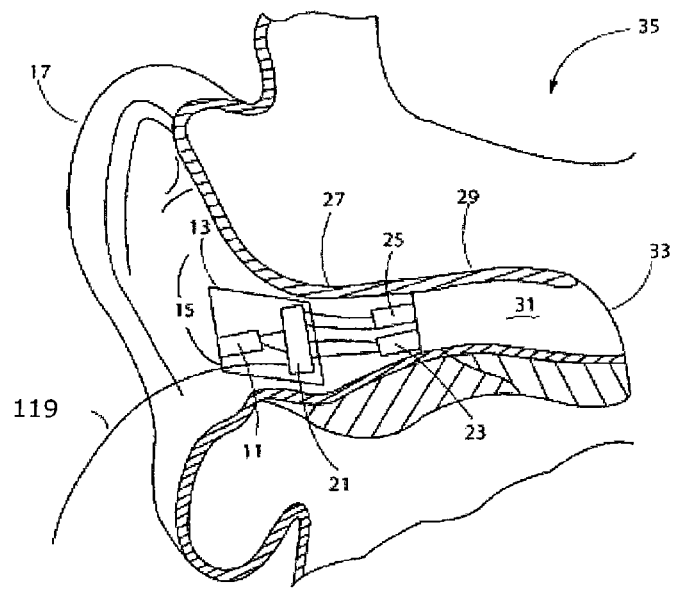
FIG. 2B is a diagram of an earpiece inserted in an ear canal of an ear of a user.

FIG. 2A illustrates various transducer configurations of an earpiece coupling to system 100 in accordance with exemplary embodiments of the invention. System 100 can be external to earpieces 41-44 or internal to the housing of an earpiece. Earpieces 41-44 illustrate non-limiting examples that can be used to attenuate sound from reaching the ear canal. Earpieces 41-44 can be an in-ear, concha, behind the ear, semi-aural, and circum-aural device. As shown, earpieces 41-44 can also provide acoustic energy to the ear canal of the user using an ambient sound microphone (ASM) 11. Having an ear canal microphone (ECM) 23 is optional in an earpiece primarily used for reducing ambient noise from reaching the ear canal such as in an industrial environment. In general, an earpiece for monitoring noise levels will have at least one transducer.

System 100 in an external housing couples through a wired connection, wireless connection or a combination of both wired/wireless connections to an earpiece. In at least one exemplary embodiment, system 100 is used to monitor sound pressure levels in a work environment and mitigate hearing damage. Earpieces 41-44 are used to reduce noise exposure to the user, generate a sound pressure level/SPL_Dose database, and take preventative measures to reduce hearing loss. The information in the database can used to ensure noise compliance and provide a safer environment for workers. Mapping of sound pressure levels or SPL_Dose is effective in identifying areas where noise exposure can be a risk to workers. Another example is a wired earpiece that is connected to a device such as a pda, cell phone, mp3 player or multi-media player through a jack or connector. System 100 couples to the sound source and the earpiece for measuring and modifying audio content presented within the ear canal. In at least one exemplary embodiment, system 100 includes connectors for connecting to the earpiece and one or more sound sources. System 100 can also connect wirelessly to the sound source and the earpiece to measure and modify audio content provided to the user of the earpiece as mentioned hereinabove.

Earpieces 41-44 are placed in or near the ear canal of the user. They can partially seal or seal the ear canal thereby creating two acoustical regions. The first region is the ear canal and the second region is ambient area in proximity to the ear. A sealing section 26 of earpieces 41-44 occludes the ear canal. Sealing section 26 can comprise a structure that blocks the opening of the ear canal such as a foam insert, flexible silicone insert, and expandable insert. An inflatable balloon is a non-limiting example of an expandable insert that will be discussed in more detail hereinbelow. In general, sealing section 26 attenuates sound from the ambient environment from entering the ear canal. As shown, earpieces 41-44 each have a speaker or transducer for providing sound to the user's ear and system 100 is shown external to each earpiece. The speaker or transducer is known as an ear canal receiver (ECR) 25. Earpiece 41 comprises a single transducer ear canal receiver 25.

Earpiece 42 comprises an ambient sound microphone 11 and ear canal receiver 25. In general, ambient sound microphone 11 receives sound from the ambient environment and can pass the signal through to ear canal receiver 25. In at least one exemplary embodiment, system 100 measures the sound pressure level of the ambient environment using ambient sound microphone 11 to include in the calculation of the sound pressure level dose received by the user.

Earpiece 43 comprises an ear canal microphone 23 and ear canal receiver 25. Similarly, earpiece 44 comprises an ear canal microphone 23 and ear canal receiver 25 plus ambient sound microphone 11. Ear canal microphone 23 of earpieces 43 and 44 receives sound local to the ear canal of the user. In at least one exemplary embodiment, system 100 measures the sound pressure level dose using ear canal microphone 23.

As disclosed hereinabove, system 100 can be attached to earpieces 41-44 to sample a signal provided to ear canal receiver 25 or measure sound pressure levels using microphones 11 and 23. System 100 receives signals intended to be provided to ear canal receiver 25, retrieves transducer information about the particular headphones worn by the user from a calibration database, and converts the signals to equivalent sound pressure level (SPL) values that is part of the SPL received by the wearer. System 100 uses calculated, measured, and estimated SPL values in accordance with the SPL Dose and/or Noise Dose equations disclosed herein, to calculate SPL Dose and/or Noise Dose values and stores the values in memory. In at least one exemplary embodiment, system 100 can send data, for example SPL, time, location, and SPL/Noise Dose values via wired or wireless communication to the earpiece, a computer, audio devices, or other devices for storage in an external database.

FIG. 2B depicts the electro acoustical assembly 13 (also referred to herein as an in-the-ear acoustic assembly 13 or earpiece 13), as it would typically be placed in the ear canal 31 of ear 17 of user 35. The assembly is designed to be inserted into the user's ear canal 31, and to form an acoustic seal with the walls 29 of the ear canal 31 at a location 27, between the entrance 15 to the ear canal and the tympanic membrane or ear drum 33. Such a seal is achieved by means of a soft and compliant housing of assembly 13. A seal is critical to the performance of the system in that it creates a closed cavity in ear canal 31 of approximately 0.5 cc in a non-limiting example between the in-ear assembly 13 and the ear's tympanic membrane 33.

As a result of this seal, the output transducer (speaker) 25 is able to generate a full range bass response when reproducing sounds for the system user. This seal also serves to significantly reduce the sound pressure level at the user's eardrum 35 resulting from the free/diffuse sound field at the entrance 15 to the ear canal 31. This seal is also the basis for the sound isolating performance of the electroacoustic assembly 13. Located adjacent to ear canal receiver (ECR) 25, is an ear canal microphone (ECM) 23, which is also acoustically coupled to closed cavity 31. ECM 23 can be used to measure the sound pressure level in cavity 31 as a part of testing the hearing sensitivity of the user as well as confirming the integrity of the acoustic seal and the working condition of itself and ECR 25. Ambient sound microphone (ASM) 11 is housed in assembly 13 and can be used to monitor sound pressure at the entrance 15 to the occluded ear canal. In at least one exemplary embodiment, transducers can receive or transmit audio signals to an ASIC 21 that acts as a transceiver for audio via the wired or wireless communication path 119.

Figure 2C:
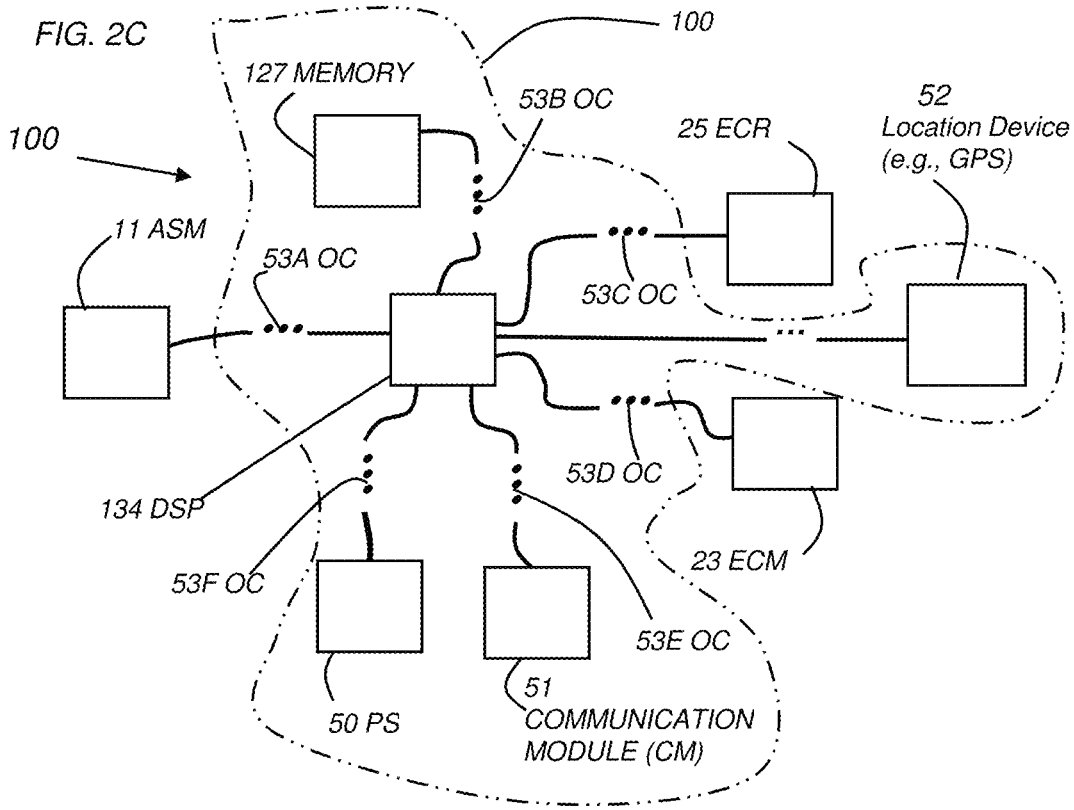
FIG. 2C illustrates various inputs and outputs that can be associated with system 100 in accordance with at least one exemplary embodiment.

FIG. 2C illustrates various inputs and outputs that can be associated with system 100. In at least one exemplary embodiment, system 100 comprises memory 127, digital signal processor 134, a communication module 51, a global positioning system (GPS) circuit 52, and a power source 50. DSP 134 has an operative connection 53A to ASM 11, an operative connection 53B to memory 127, an operative connection 53C to ECR 25, an operative connection 53D to ECM 23, an operative connection 53E to communication module 51 and an operative connection 53F to power supply 50. As disclosed previously, the operative connections can be wired or wireless. The components of system 100 can also be in one or more housings remote to the earpiece of the user. It should be understood that ASM 11 couldn't be too remote from the ear of the user in order to properly measure the ambient sound and ambient environment.

ECM 23 can be used to measure the noise level as it exists in inner ear canal 31. This includes ambient sound as attenuated by the earpiece and/or any sound produced by ECR 25 from one or more sound sources or from ASM 11. In at least one exemplary embodiment, DSP 134 can make use of controls, weighting curves, and stored values in order to process the acoustic signals detected by ECM 23. Total SPL_Dose is a function of both ambient noise and any driving signals delivered to ECR 25 from a connected personal media device such as a cell phone or music player. Thus, system 100 can be attached or coupled to either the earpiece or to audio devices.

In the above description the operation of system 100 is driven by sound pressure level, i.e. sound levels are monitored for time periods or epochs during which the sound pressure level does not equal the minimum level threshold or is constant. However, as will be discussed in connection with the next exemplary embodiments of the invention, system 100 can also operate utilizing fixed or variable sampling epochs determined as a function of one or more of time and changes in sound pressure level, sound pressure level dosage, weighting functions to the sound pressure level, and restorative properties of the ear.

Figure 2D:
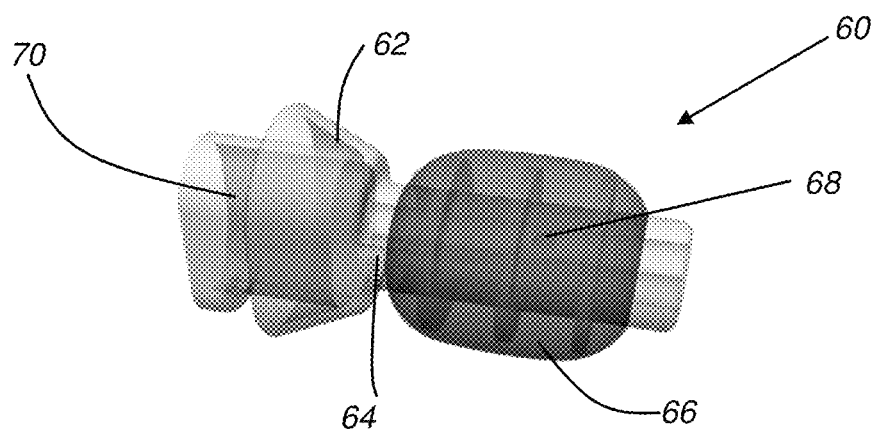
FIG. 2D illustrates an inflatable system comprising an insertion element and an expandable element in accordance with at least one exemplary embodiment.

FIG. 2D illustrates an inflatable system 60 comprising an insertion element 64 and an expandable element 68. In at least one exemplary embodiment, inflatable system 60 is a sealing section for earpieces 41-44. Insertion element 64 can be a multi-lumen tube for acoustic coupling to the ear canal and for delivering an expanding medium to expandable element 68. For example, insertion element 64 can have a first lumen acoustically coupled to ear canal receiver 25, a second lumen acoustically coupled to ear canal microphone 23, and a third lumen coupled to a pump for inflating expandable element 68. The first and second lumen each have a port on the distal end of insertion element 64 that acoustically couples to the ear canal when an earpiece is worn by the user.

In at least one exemplary embodiment, expandable element 68 comprises a balloon made of a material such as urethane, silicone, or nylon. Other flexible and non-flexible materials could also be used that are comfortable, provide sufficient attenuation for mitigating hearing damage, and minimize the occlusion effect. Expandable element 68 can be filled with an expanding medium 66 such as gas, liquid, electroactive polymer, or gel. Expandable element 68 can be inflated utilizing an active or manual pump. Expandable element 68 is expanded until the ear canal is sealed. Thus, the system can accommodate multiple ear canal sizes. Conversely, the expanding medium 66 can be vented or removed from the expandable element to a reservoir to reduce the size of expandable element 68 prior to when the sealing section is removed from the ear.

The sealing section further includes a flange 62 designed to stop at a designated position in the ear canal. For example, flange 62 is made larger than the largest ear canal opening (or a size that covers the majority of the population) to prevent insertion beyond the length of insertion element 64. Insertion element 64 is designed for a length shorter than the shortest ear canal length (or a length that cover the majority of the population) to prevent touching the tympanic membrane or the ear canal. An instrument package 70 is used to hold additional devices, circuits, and equipment to support expansion control or other earpiece functions (e.g. transducers, signal processing). In general, instrument package 70 is a housing within the earpiece.

Figure 3:
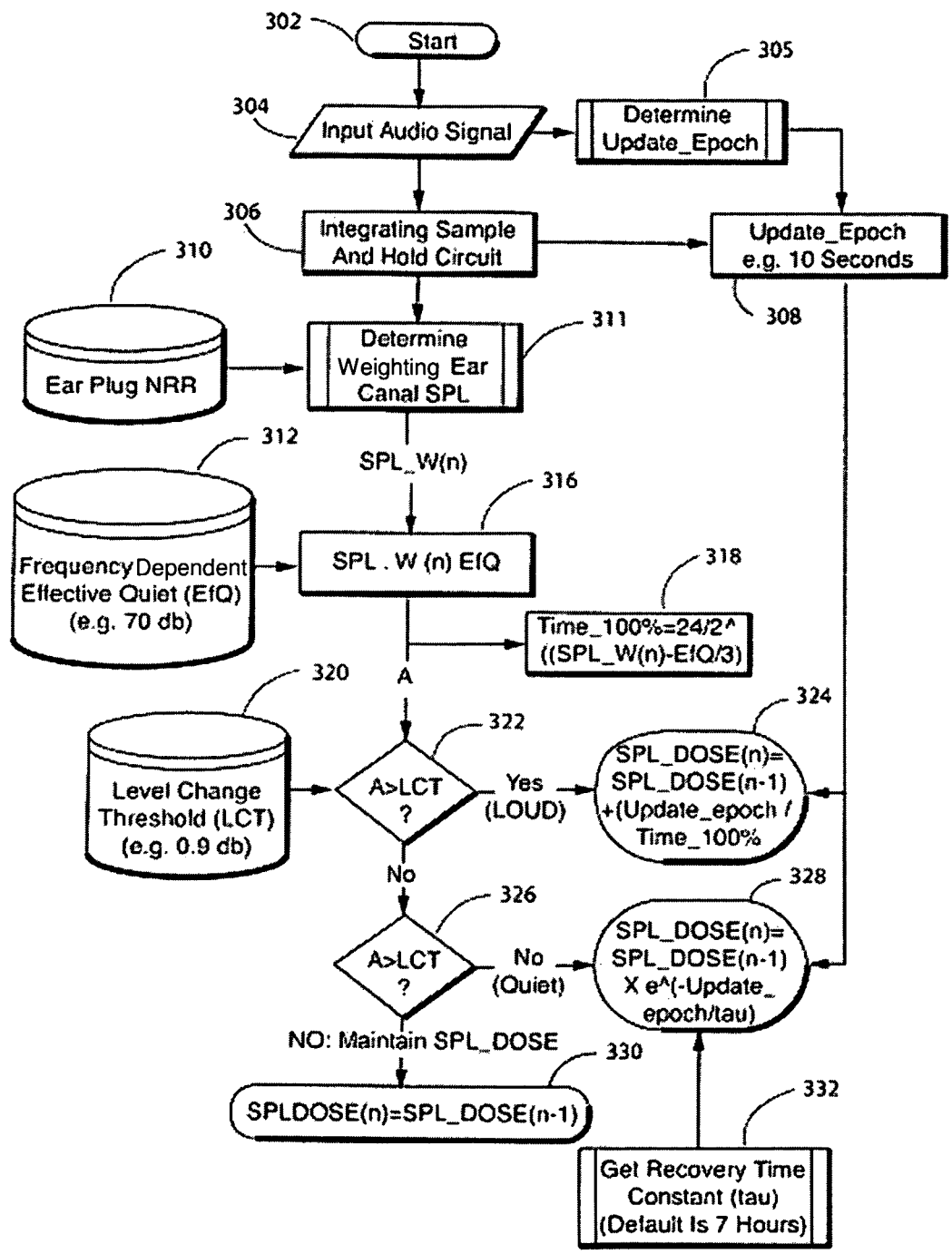
FIG. 3 is a flow chart for calculating listening fatigue, in accordance with at least one exemplary embodiment of the invention, which measures a quantity (e.g., the sound pressure level) over time as received at the ear.

Reference is now made to FIG. 3 in which a flow chart for monitoring the sound pressure level dose at various sample times n is provided. The process is started in a step 302. An input audio signal is generated in a step 304 at either the ear canal microphone (ECM) 23, the ambient sound microphone (ASM) 11, a microphone on system 100, or by monitoring one or more sound source signals. Changes in SPL_Dose resulting from duration of exposure time is a function of the sound pressure level (corresponding to the input audio signal), therefore, the epoch or time period used to measure ear exposure or, more importantly, the time-period for sampling sound pressure level is determined in a step 305. The update epoch is used in the SPL_Dose function determination as well as to effect the integration period for the sound pressure level calculation that, as will be discussed below, is used to calculate the weighted ear canal sound pressure level.

Figure 6:
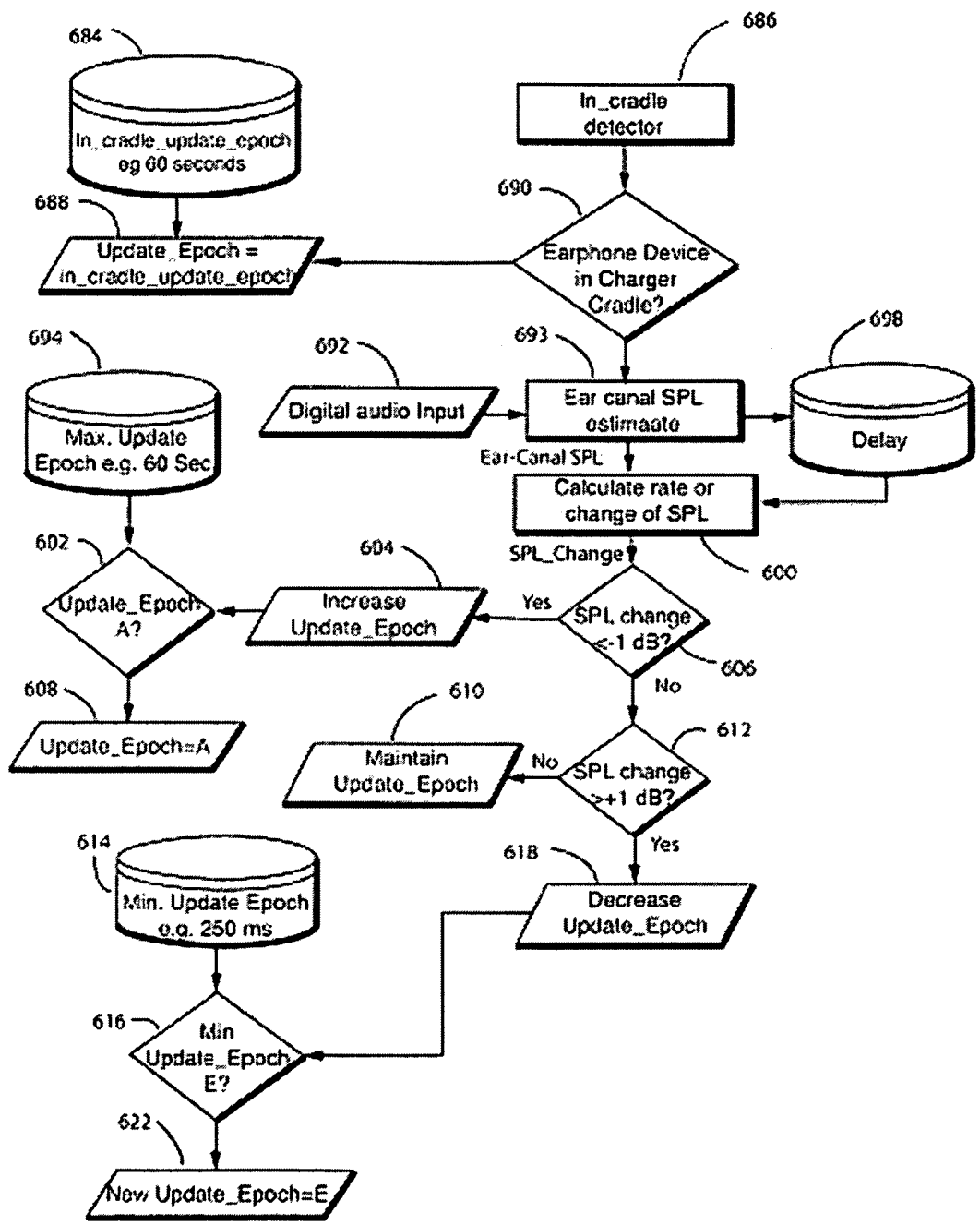
FIG. 6 is a flow chart for determining an update epoch in accordance with at least one exemplary embodiment of the invention.
Figure 7:
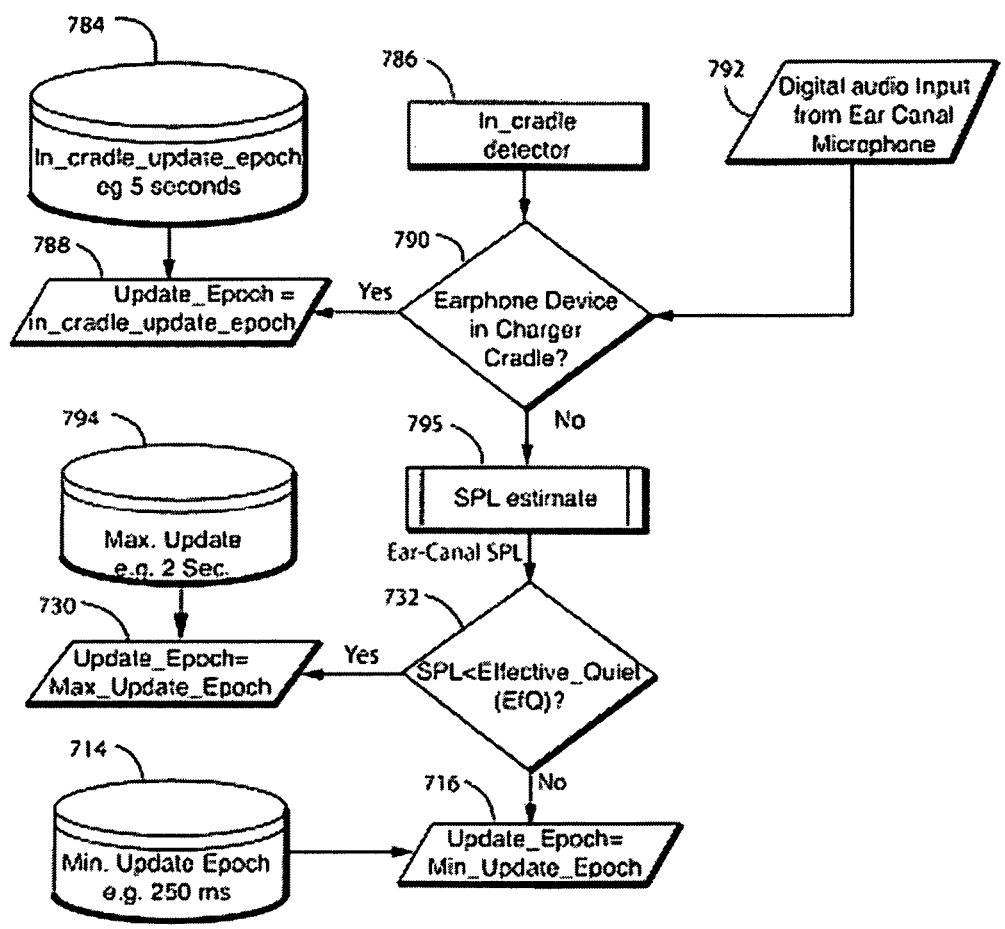
FIG. 7 is a flow chart for determining an update epoch in accordance with at least one exemplary embodiment of the invention.

Reference is now made to FIGS. 6 and 7. In FIG. 6, a method is defined to change the update epoch as a function of the weighted ear canal sound pressure level, which will be discussed in greater detail below. In at least one exemplary embodiment, system 100 is capable of determining when earpiece 13 is not in use, in a charger or communication cradle since it is operatively coupled to the device. In a step 684, a predetermined standard is provided for the update epoch, 60 seconds in this example. In step 688, the update epoch is set as the in-cradle update epoch. The in-cradle state is detected in a step 686. If it is determined in a step 690 earpiece 13 (also referred to herein as earphone device 13) is in a charger or cradle mode, then the update epoch is set as the in-cradle epoch; in the step 688.

However, if in step 690 it is determined that the earphone device 13 is in use, in other words "not in the cradle", then, by default, an audio signal is input to earpiece 13 in step 692. In step 693, an ear canal sound pressure level is estimated as a function of the audio input at step 692. The current (n) ear canal sound pressure level estimate is stored as a delay level in a step 698. An audio input is determined at a later time when step 692 is repeated so that a second in-time ear canal sound pressure level estimate is determined.

In a step 600, the delayed (n−1) or previous sound pressure level is compared with the current (n) ear canal sound pressure level estimate to calculate a rate of change of the sound pressure level. The change level is calculated in units of dB per second. This process of step 692 through 600 is periodically repeated.

In a step 606, it is determined whether or not the sound pressure level change is less than a predetermined amount (substantially 1 dB by way of non-limiting example) between iterations, i.e., since the last time the ear canal sound pressure level is calculated. If the change is less than the predetermined amount, then in step 604 the update epoch is increased. It is then determined in a step 602 whether or not the epoch update is greater than a predefined amount D set in step 694 as a maximum update epoch such as 60 seconds in a non-limiting example. If in fact, the update epoch has a value greater than the maximum update epoch D then the update epoch is set at the higher value D in step 608.

If it is determined in step 606 that the sound pressure level change is, in a non-limiting example, greater than −1 dB, but less than +1 dB as determined in step 612, then the update epoch value is maintained in a step 610. However, if it is determined that the sound pressure level change is, in a non-limiting example, greater than +1 dB, then the update epoch value is decreased in a step 618 to obtain more frequent sampling. A minimum predetermined update epoch value such as 250 microseconds is set in a step 614. If the decreased update epoch determined in step 618 is less than, in other words an even smaller minimum time-period than the predetermined minimum update epoch E, then the new update epoch is set as the new minimum update epoch value in steps 616 and 622. In this way, the sample period is continuously being adjusted as a function of the change in sound pressure level at the ear. As a result, if the noise is of a transient variety as opposed to a constant value, the sampling interval will be changed to detect such transients (e.g., spikes) and can protect the ear.

Reference is now made to FIG. 7 in which a method for changing the update epoch is illustrated as a function of the way that the ear canal sound pressure level estimate is provided. Again, in accordance with at least one exemplary embodiment of the invention, the update epoch is decreased when the ear canal sound pressure level is high or increasing.

The difference between the embodiment of FIG. 7 and the embodiment of FIG. 6 is that the update epoch is not continuously adjusted, but is more static. If the ear canal sound pressure level is less than PSL (e.g., effective quiet, a decibel level which when the ear is exposed to over time does not damage or facilitate restoration the ear), then the update epoch is fixed at a predefined maximum epoch value and this is the value used by system 100 as will be discussed in connection with FIG. 3. In this embodiment, a system for monitoring sound pressure levels at the ear includes an ambient sound microphone for receiving ambient sounds and an ear canal microphone for producing audio signals as a function of ambient sound received at the ambient sound microphone and a sound signal received from an associated personal audio device. A logic circuit is operatively associated with the ASM and calculates a Total SPL_Dose experienced by the ear at a time t.

In one exemplary embodiment the Total SPL_Dose is calculated by determining estimated SPL_Dose for time periods Δt. The logic circuit may then select an action parameter in response to the Total SPL_Dose. If it is determined to be greater than a permissible (or permitted) sound level (PSL) (e.g., effective quiet), then the update epoch is fixed at a shorter minimum value and this is returned as the update epoch to be utilized.

In FIG. 7, specifically, as with FIG. 6, an in-cradle update epoch of 5 seconds by way of non-limiting example, is stored in system 100 in a step 784. In a step 788, the initial update epoch is set as the in-cradle update epoch. A maximum update epoch time, such as 2 seconds by way of non-limiting example, is stored in a step 794. In a step 714, an initial minimum update epoch (250 microseconds in this non-limiting example) is stored.

In a step 786 and step 790 it is determined whether or not system 100 is in a non-use state, i.e., being charged or in a cradle. If so, then the update epoch is set at the in-cradle update epoch. If not, then a digital audio signal is input from ear canal microphone 23 in step 792. A sound pressure level is estimated in step 795. It is then determined whether or not the ear canal sound pressure level is less than PSL (e.g., effective quiet) in a step 732. If the sound pressure level is less than the PSL (e.g., effective quiet) as determined in step 732, then the update epoch is set at the maximum update epoch in a step 730. If the sound pressure level is more intense than the effective quiet, then in step 716, the update epoch is set to the minimum update epoch.

Returning to FIG. 3, in a non-limiting exemplary embodiment, the update epoch is set at 10 seconds in a step 302 utilizing either a constant predetermined sample time, or either of the methodologies discussed above in connection with FIGS. 6 and 7. In a step 306, the input audio signal is sampled, held, and integrated over the duration of the epoch as determined in step 308. As a result, the update epoch affects the integration period utilized to calculate the sound pressure level dose as a function of the sound pressure level and/or as the weighted ear canal sound pressure level.

In a step 310, an earplug noise reduction rating (NRR) is stored. The noise reduction rating corresponds to the attenuation effect of earpiece 13, or system 100, on sound as it is received at audio input 11 and output at the output transducer 25 or as it passes from the outer ear to the inner ear, if any exemplary embodiment has no ambient sound microphone 11. In a step 311, a weighted ear canal sound pressure level is determined, partially as a function of the earplug noise reduction rating value.

Figure 4:
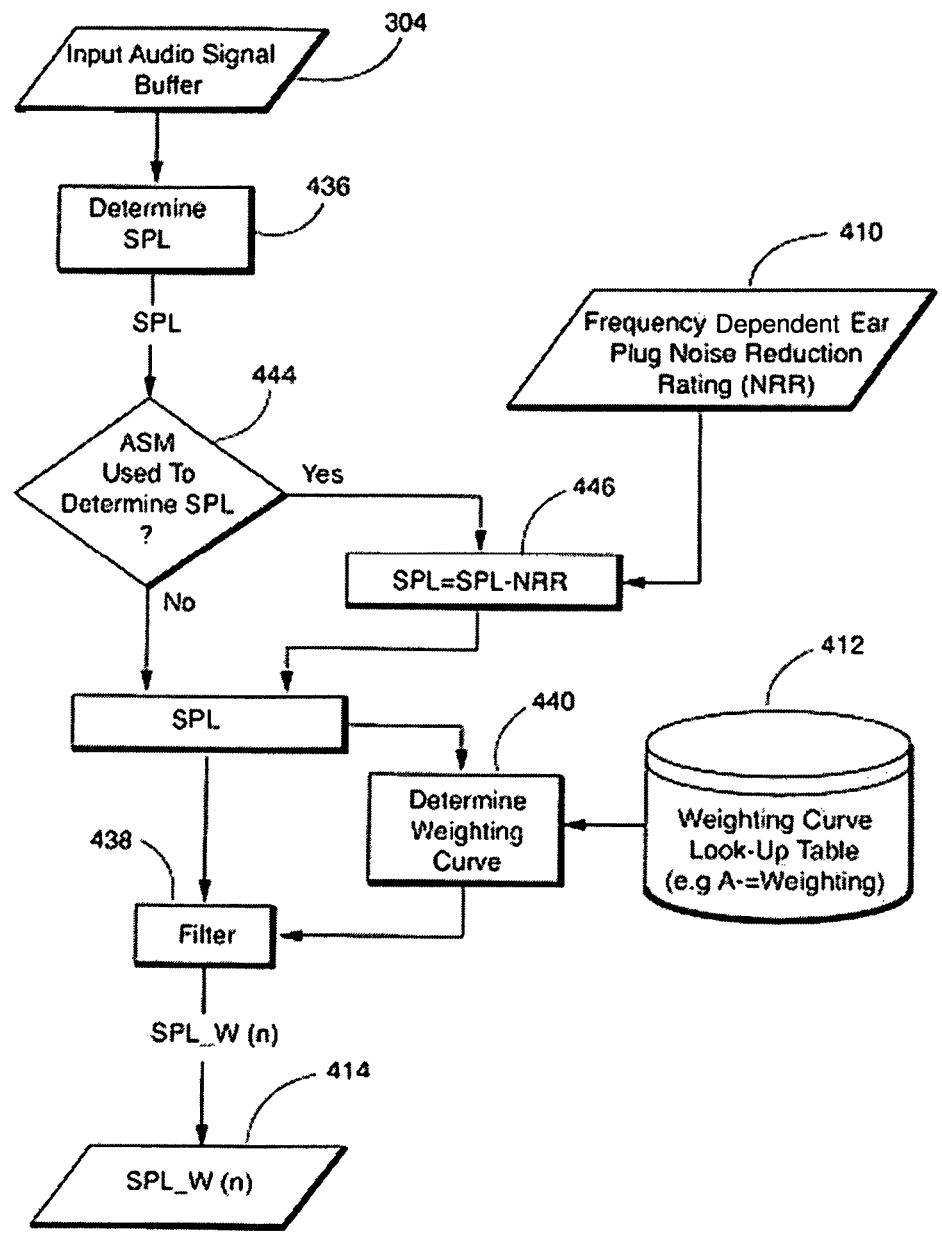
FIG. 4 is a flow chart for determining a weighted ear canal sound pressure level in accordance with at least one exemplary embodiment of the invention.

Reference is now made to FIG. 4 where a method for determining the weighted ear canal sound pressure level in accordance with at least one exemplary embodiment of the invention is illustrated. Like numerals are utilized to indicate like structure for ease of discussion and understanding. Weighting is done to compensate for the manner in which sound is perceived by the ear as a function of frequency and pressure level. As sounds increase in intensity, the auditory perception of loudness of lower frequencies increases in a nonlinear fashion. By weighting, if the level of the sound in the sound field is low, the methodology and system utilized by at least one exemplary embodiment of the invention reduces the low frequency and high frequency sounds to better replicate the sound as perceived by the ear.

Specifically, a weighting curve lookup table, such as A-weighting, acts as a virtual band-pass filter for frequencies at sound pressure levels. In a step 304, the audio signal is input. In step 410, frequency-dependent earplug noise reduction ratings are stored. These values are frequency-dependent and in most cases, set as manufacturer-specific characteristics.

As discussed above, in a step 306, the input audio signal is shaped, buffered and integrated over the duration of each epoch. The sound pressure level of the shaped signal is then determined in a step 436. It is determined whether or not ambient sound microphone (ASM) 11 was utilized to determine the sound pressure level in a step 444. If microphone 11 was utilized, then the frequency-dependent earplug noise reduction rating of earpiece 13 must be accounted for to determine the sound level within the ear. Therefore, the noise reduction rating, as stored in step 310, is utilized with the sound pressure level to determine a true sound pressure level (at step 446) as follows:

$$SPL_{ACT} = SPL - NRR: \quad (3)$$

where sound pressure $SPL_{ACT}$ is the actual sound pressure level received at the ear medial to the ECR, SPL is the sound pressure level determined in step 436 and NRR is the noise reduction rating value stored in step 410.

If the ambient sound microphone (ASM) 11 is not used to determine the sound pressure level then the sound pressure level determined in step 436 is the actual sound pressure level. So that:

$$SPL_{ACT} = SPL \quad (4)$$

It is well within the scope of at least one exemplary embodiment of the invention to utilize the actual sound pressure level as determined so far to determine the affect of the sound pressure level received at the ear on the health of the ear. However, in at least one exemplary embodiment, the sound pressure level is weighted to better emulate the sound as received at the ear. Therefore, in a step 412, a weighting curve lookup table is stored within system 100. In a step 440, the weighting curve is determined as a function of the actual sound pressure level as calculated or determined above in steps 436, 446 utilizing a weighting curve lookup table such as the A-weighting curve. The A-weighting curve is then applied as a filter in step 438 to the actual sound pressure level. A weighted sound pressure level value representative of a sampled time period (SPL_W(n)) is obtained to be utilized in a step 414.

The weighting curve can be determined in step 440 by applying a frequency domain multiplication of the sound pressure level vector and the weighting curve stored in step 412. In this exemplary embodiment, the weighting curve would be appropriate for direct multiplication with the SPL in the frequency domain (i.e., SPL(f)). In another exemplary embodiment the weighted SPL can be expressed as a weighting of the measured pressure vector as:

$$\text{SPL\_W}(n)(t) = 20\log\left(\frac{\Delta P^{W_A}(t)}{\Delta P_0}\right) \quad (5)$$

where ΔP(t) is the measured temporal change in root mean squared pressure, which can be converted into spectral space (e.g., FFT) as ΔP(f) which is the measured spectral change in pressure, which can in turn be multiplied by a weighting function (e.g., A-weighting), $W_A(f)$ and expressed as $\Delta P^{W_A}(f) = \Delta P(f) \cdot W_A(f)$–, and then reconverted (e.g., inverse FFT) into temporal space to obtain $\Delta P^{W_A}(t)$. To obtain a single value various integration or summation over the n-th time interval (e.g., which can change in time) can be performed. For example:

$$\text{SPL\_W}(n) = \frac{1}{\Delta t_n}\int_{t_{n-1}}^{t_n} 10\log\left(\frac{(\Delta P^{W_A}(t))^2}{\Delta P_0^2}\right)dt \quad (6)$$

The time during which a user may be exposed to the sound level SPL_W(n), i.e. the time to 100% allowable dosage at SPL level SPL_W(n), is referred to below as Time_100% (n).

The weighting curves can be stored as a lookup table on computer memory, or can be calculated algorithmically. Alternatively, the input audio signal can be filtered with a time or frequency domain filter utilizing the weighting curve stored in step 412 and the sound pressure level as calculated. For low-level sound pressure levels, those less than 50 dB, by way of non-limiting example, a weighting curve, which attenuates low and high frequencies can be applied (similar to an A-weighting curve). For higher sound pressure levels, such as more than 80 dB, by way of non-limiting example, the weighting curve can be substantially flat or a C-weighting curve. The resulting weighted ear canal sound pressure level during any respective sampling epoch is returned as the system output SPL_W(n) in step 414. Note that herein various conventional weighting schemes are discussed (e.g., A-weighting, C-weighting) however in at least one exemplary embodiment non-conventional weighting schemes can be used. For example, generally the threshold level of hearing sensitivity (threshold of detection) is referenced in dB, where 20 micropascals is typically used as the minimum threshold level of pressure variation that an average normal-hearing person can detect. This reference value tends to be used at all frequencies, although the threshold level varies with frequency. Thus, one weighting scheme is to adjust the reference 0 dB level on a frequency basis, by using a conventional dB of threshold hearing chart, which provides the dB (f) at threshold level. A weighting function can be used where the value is about 1 at the reference value (e.g., equivalent to 20 micropascals) at a reference frequency (e.g., 1000 Hz). The other values (e.g., as a function of frequency) of the weighting function can vary depending upon the reference threshold pressure variation for the particular frequency, for example if at 30 Hz the threshold level in dB is 65 dB, then the weighting value can be 1/65 at 30 Hz, de-emphasizing the loudness and/or intensity at 65 dB when SPL_Dose (f) is calculated.

Returning to FIG. 3, a safe listening time is calculated by comparing the weighted sound pressure level with the PSL (e.g., effective quiet level) in step 316. Therefore, a value A corresponding to how far from safe listening the sound pressure level is, is determined by the equation:

$$A = \text{SPL\_W}(n) - \text{PSL} \quad (7)$$

where PSL is the permissible sound level, for example PSL=EfQ, where EfQ is equal to the sound level of effective quiet (as stored at step 312). However, PSL can be any level chosen for the particular circumstance, for example lower than EfQ.

By utilizing this simple comparative function, fewer machinations and processes are needed. System 100 takes advantage of the fact that because the PSL (e.g., effective quiet level) can be neutral to the ear, sound pressure levels significantly above the PSL (e.g., effective quiet level) are generally damaging and noise levels below the PSL (e.g., effective quiet) generally allow for restoration/recovery.

In step 318, the remaining safe listening time at the beginning of any current sampling epoch can be calculated by Time_100% minus the time duration of exposure up to the current sampling epoch. Note that a negative number can occur, indicating that no safe listening time remains. The estimated time (e.g., in hours) until the individual's sound exposure is such that permanent threshold shift may occur, ignoring any previous sound exposure and assuming that the SPL of the sound field exposed to individual remains at a constant level L can be calculated as follows:

$$\text{Time\_100\%}(n) = T_c(2^{((\text{SPL\_W}(n)-\text{PSL})/\text{ER})}); \quad (8)$$

where PSL is the permissible sound level, and Tc is the critical time period. For example, if Tc (Critical Time) is 8 hours and PSL is 90 dBA and ER (the Exchange Rate) is 5 dB, then that accepts that ~22-29% of people are at risk for hearing loss. If Tc is 8 hours and PSL is 85 dBA and ER is 3 dB, then that accepts that ~7-15% of people are at risk, likewise for if Tc is 24 hours and PSL is 80 dBA and ER is 3 dB, same 7-15% at risk. Thus, Time_100% (n) reflects a reduction of the risk to a chosen level. Note that $T_c$ is the critical time period of exposure that one is looking at (e.g., 8 hours, 24 hours), and ER is the exchange rate, for example can be expressed as:

$$\text{Time\_100\%}(n) = 8 \text{ (hours)}/(2^{((\text{SPL\_W}(n)-85 \text{ dBA})/3 \text{ dB})}) \quad (9)$$

These values assume a recovery period of 16 hours at a SPL during that time of less than 75 dBA (where dBA refers to Decibels of an A-weighted value). Of course the realism of such an assumption is questionable given music, TV, and other listening habits of individuals. Thus, we are concerned with exposure over a 24-hour period. Thus, Time_100% (n) can be expressed for a 24 hour period (e.g., $T_c$=24 (hours)), where, for example using an equal energy assumption (i.e., ER of 3 dBA), as:

$$\text{Time\_100\%}\ (n) = 24/(2^{((SPL\_W(n)-PSL)/3)}). \qquad (10)$$

Another further example is the situation where PSL=EfQ, where the Effective Quiet, EfQ is defined as the highest sound level that does not cause temporary or permanent hearing threshold shift, nor does it impede recovery from temporary hearing threshold shift. For broadband noise, it can be 76-78 dBA, although these numbers can be different or refined over time based upon research and/or measurement history.

As a non-limiting example, the lower bound of SPL_W(n) dictating the Time_100% equation would be SPL_W(n)= PSL, and the upper bound of the SPL_W(n) dictating Time_100% equation would be about SPL_W(n)=115 dB.

Note that in at least one exemplary embodiment, the acoustic signals measured by an ECM or an ECR in ECM mode, can be used to detect a user's voice, for example using the technology discussed in Webster et al., U.S. Pat. No. 5,430,826, incorporated by reference in its entirety. If voice is detected then by the magnitude of the SPL (e.g., 80 dB) one can tell whether the user is speaking as compared to a non-user's voice (e.g., 50 dB) that has been attenuated by the earpiece. When a user's voice is detected then SPL_W(n) can be reduced by an amount (DSPL, e.g., 20 dB) that is due to Stapedius (Middle-ear Muscle) Reflex (e.g., when the user's voice triggers a muscle response in the muscles supporting the ossicles transmitting sound from the eardrum to cochlea), effectively damping some of the sound. Thus $SPL\_W(n)_{new}$=SPL_W(n)-DSPL, where $SPL\_W(n)_{new}$ is used in the Time_100% (n) equation as opposed to SPL_W (n).

In this embodiment, rather than make use of the Sound Level (L), the period is a function of the intensity (both high and low) of the weighted sound pressure level. It should be noted that PSL (e.g., effective quiet) is used in the above example, but any level of interest, such as 80 dB, or no sound level, i.e., SPL_W(n)–0, can be used. The weighted sound pressure level and PSL can be expressed as a frequency-dependent numerical array or a value scalar.

It is next determined whether or not the difference between the current weighted sound pressure level and the PSL (e.g., effective quiet) is above a tolerable threshold for risk of hearing damage or not, i.e., whether the weighted SPL in the eardrum is considered to increase risk for hearing damage or not. A sound pressure level dose is calculated depending upon whether the sound level is sufficiently intense or not. The sound pressure level dose (SPL_Dose) is the measurement, which indicates an individual's cumulative exposure to sound pressure levels over time. It accounts for exposure to direct inputs such as MP3 players, phones, radios and other acoustic electronic devices, as well as exposure to environmental or background noise, also referred to as ambient noise. The SPL_Dose is expressed as a percentage of some maximum time-weighted average for sound pressure level exposure.

Because the sound pressure level dose is cumulative, there is no fixed time-period for ear fatigue or damage. At or below effective quiet, the sound pressure level exposure time would theoretically be infinite, while the time period for achieving the maximum allowable sound pressure level dose becomes smaller and smaller with exposure to increasingly more intense sound. A tolerable level change threshold corresponding to the amount of noise above or below the effective quiet, which has no great effect on the ear as compared to effective quiet, is determined and stored in memory 127 in a step 320. In a step 322, the differential between the weighted sound pressure level and the effective quiet is compared to the level change threshold.

A differential value A, corresponding to the level change, can be calculated as follows:

$$A = SPL\_W(n) - PSL \qquad (11)$$

If A is greater than the level change threshold, the noise is considered to increase risk for hearing damage and the sound pressure level dose is calculated in a step 324 as follows:

$$\text{SPL Dose}(n) = \text{SPL Dose}(n-1) + (\text{Update\_Epoch}(n)/\text{Time\_100\%}) \qquad (12)$$

where SPL Dose(n-1) is the SPL Dose calculated during the last epoch; Update_Epoch is the time (in hours) since the last SPL Dose was calculated. As described above, Update_Epoch can be adaptive, e.g., shortened when the sound pressure level is higher; and Time_100% (n), the time period remaining for safe exposure is determined by the equation:

$$\text{Time\_100\%}\ (n) = 24\ \text{hours}/(2^{((L-PSL)/3)}) \qquad (13)$$

where L=sound level (in dB) of the combination of environmental noise and audio playback. It should be noted that sound level (L) can be substituted for SPL_W(n).

It should be noted, as can be seen from the equation, that the time value becomes more important than the sound pressure level as updates are spread apart. However, this is to protect overexposure to harmful sounds because a less accurate sample size must account for the unknown. The wider the periodicity, the less accurate determination of actual exposure. Infrequent updates of the SPL Dose assume a relatively constant sound level, ignoring transients (e.g. spikes) and intervening restorative periods. Accordingly, sound pressure level and epoch periodicity are weighed against each other to protect the ear.

If in step 322 it is determined that the differential is not greater than the level change threshold, including negative values for A (which are restorative values), then in step 326 it is determined whether or not the differential, as determined in step 316, is less than the level change threshold in a step 322. If it is determined that the differential is not less than the level change threshold, then the received noise was the effective quiet level, i.e., the level change threshold equals zero and in a step 330, the current SPL Dose is maintained at the same level. There is no change to the dose level. However, if the differential A is less than the level change threshold then this is a restorative quiet as determined in step 326. Thus, if the differential A (e.g., A=SPL_W(n)-PSL) is less than zero, within measurement error, then this is considered a restorative quiet, then the n-th SPL dose is determined as $$\text{SPL Dose}(n) = \text{SPL Dose}(n-1) * e^{(-\text{Update\_epoch}/\tau)} \qquad (14)$$

where: τ (referred to as "tau" in the following diagrams) can vary (e.g., equal to about 7 hours). In some exemplary embodiments, tau is adaptive for different users. In at least one exemplary embodiment, the level change threshold (e.g., measurement error) is set at substantially 0.9-1.0 dB.

Note that other forms of a recovery function can be used and the description herein is not intended to limit the recover function to an exponential relationship. For example, during lower exposure times (e.g., 102 minutes) some SPL values (e.g., 95 dB) can be used, if the subsequent SPL is less than PSL, in a linear manner (for example linearly decreasing until there is a near zero threshold shift at 4000 Hz after one day from the time at which SPL<PSL).

Another non-limiting example of a recovery function can be a combination over certain exposure and decay periods (e.g., 7 day exposure at 90 dB, with an initial threshold shift after the 7 days of about 50 dB at 4000 Hz). For example a slow decaying linear relationship can be applied for the first few hours (e.g., 2 hours) where SPL<PSL, then an exponential decay from after the first few hours to a few days (e.g., 4 days) after which a leveling trend can occur.

Additionally, although a fractional increase in SPL Dose is given as a non-limiting example, SPL Dose increase can be linear or exponential depending upon the exposure SPL level and the duration. For example the growth can be linear at certain SPL values (e.g., 95 dB) during different ranges of exposure time (e.g., for 95 dB, from about 4 minutes to 12 hours), then leveling out (e.g., threshold shift of about 59.5 dB) when the exposure time exceeds a certain length (e.g., for 95 dB about 12 hours).

In at least one exemplary embodiment the SPL values measured by an ECM (e.g., in an ECM mode) can be modified by a modification value (e.g., additive or multiplicative), for example $SPL_{new} = \beta SPL_{old} + \delta$, where the values, $\beta$ and $\delta$, can be time variant, positive or negative. Alternatively the values can be applied to the measured pressure values in a similar manner. One can convert the SPL measured by an ECM to free field values, which then can be compared to free field standards for damage risk criteria. For example Table 1 lists several frequency dependent responses of an earpiece while inserted, the "A" weighting curve offset, and the modification values $\beta$ and $\delta$.

TABLE 1

| Freq. (Hz) | Earpiece Freq. Resp. (dBSPL/V) | "A" weight offset (dB) | β (dB) | δ (dB) |
|---|---|---|---|---|
| 100 | 95 | −19.1 | 1.0 | 0.00 |
| 500 | 103.5 | −3.2 | 1.0 | −0.13 |
| 1000 | 104.0 | 0.0 | 1.0 | −1.83 |
| 2000 | 121.0 | 1.2 | 1.0 | −7.84 |
| 4000 | 106.0 | 1.0 | 1.0 | −15.57 |

Thus, for example an SPL (f) measured at 80 dB, at f=1000 Hz, would be subtracted by −1.83 to obtain a free field value to compare with damage-risk criteria, thus obtaining an $SPL_{new}$ of 78.13 dB. Note what is described is a non-limiting example, various other earpieces can have different values, and the SPL_DOSE equations, described herein, (e.g., SPL_Dose(n), Time_100%) can be based upon $SPL_{new}$. Note that further discussions concerning frequency responses and free field estimate (FFE) conversion can be viewed in U.S. Pat. No. 6,826,515, Bernardi et al. Alternatively ear canal dBA SPL (e.g., as measured by an ECM) may be converted to FFE dBA SPL using Table 1 of ISO 11904-1 (2002), incorporated herein by reference.

In step 332, the recovery time constant tau is determined. It may not be a function of exposure, but rather of recovery. It can be a default number or be determined as will be discussed below. As the SPL Dose is calculated by system 100, it is also monitored. Once the SPL Dose reaches a certain level, as it is a cumulative calculation, ear fatigue calculator 130 determines whether or not the SPL Dose corresponds to a fatigued ear, and if so, it outputs warnings as discussed in connection with FIG. 1.

Figure 5:
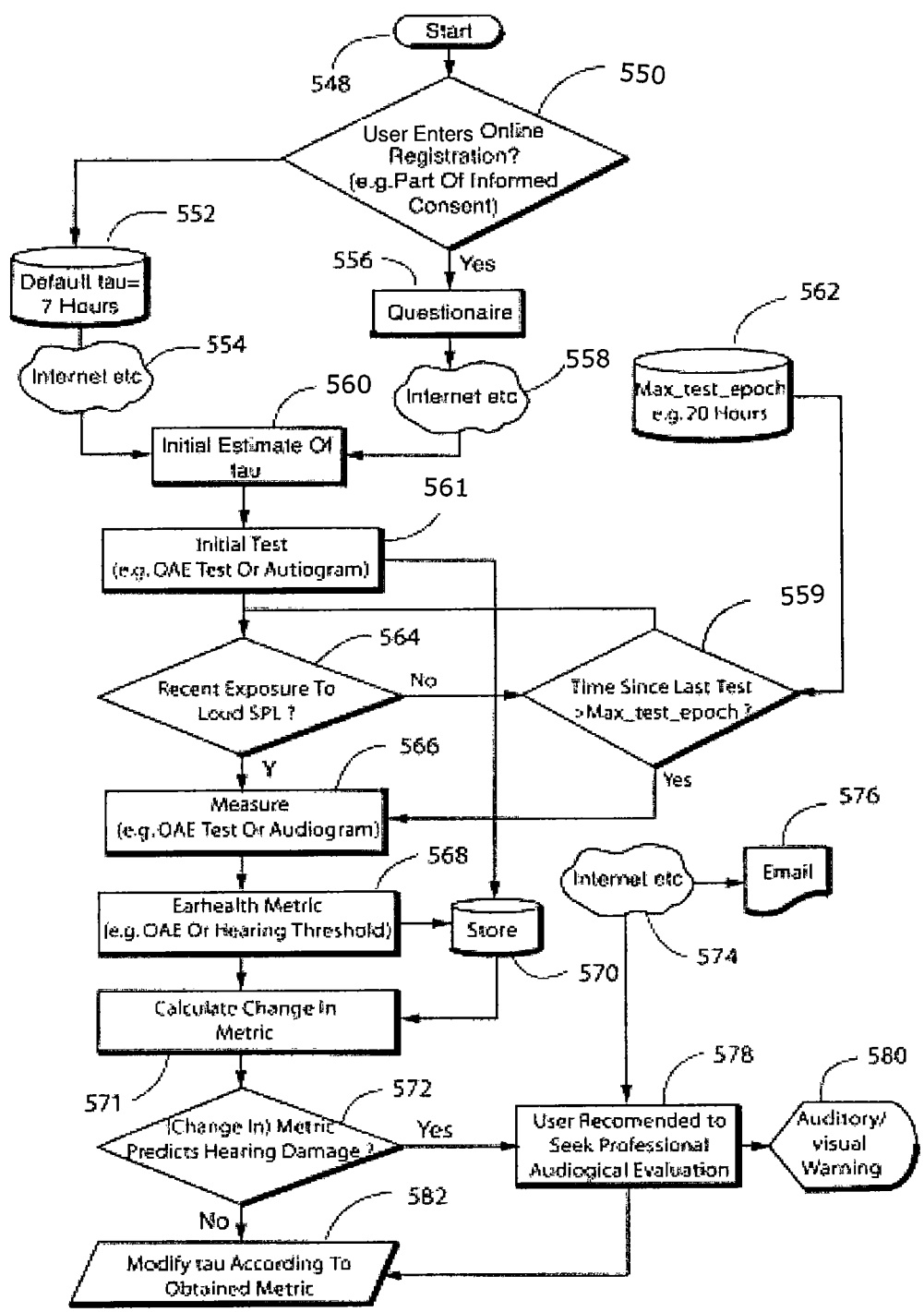
FIG. 5 is a flow chart for determining a personalized recovery time constant in accordance with at least one exemplary embodiment of the invention.

Reference is now made to FIG. 5 which depicts an optional methodology for not only updating the recovery time constant (tau) for individual users, but to provide additional methods for acting upon detected damaging exposure. The process is started at a step 548. In a step 550, it is determined whether or not the user wishes to make use of a registration process, for example online, for setting a personalized update epoch through communication with a remote registration system. If the user declines the registration, then the default tau is set at 7 hours in a step 552. In a step 554, this default value is transmitted to system 100 via a wired or wireless data communication network.

Alternatively, if the user registers in step 550, a questionnaire is presented in a step 556 in which the user informs system 100 regarding a user sound exposure history, age, work habits and other personal details that could affect the user's personal recovery function time, i.e., the time constant tau. The individual characteristics can be input to a formula or utilized as part of a look up table to determine the tau for the individual user. The estimate of tau determined in step 556 is transmitted to system 100 via a wireless or wired data communication system in a step 558. In step 560, the initial estimate of tau is set from the value determined in step 556.

An initial hearing test is performed in a step 561, which acquires data indicative of the user's hearing sensitivity and/or auditory function. The test may be an otoacoustic emission (OAE) test or audiogram administered utilizing the ear canal receiver 25. However, the test can also be administered over the Internet, telephone or other communication device capable of outputting sounds sent across a distributed network and enabling responsive communication. The data is stored in a computer memory as an initial test value in a step 570 and is used in further processing to detect a change in the user hearing response.

In a step 564, it is determined whether the user has been recently exposed to intense sound pressure levels. This can be done utilizing the sound pressure level dose as stored or permanently calculated by system 100. If it is decided in step 564 that the user's ear canal sound pressure level is low, then in a step 559 it is determined whether the time since the last test is greater than a maximum test epoch. At the outset, the maximum test epoch is a set number determined in a step 562. In this non-limiting example, the maximum test epoch is set at 20 hours.

If it is determined that the time since the last test is greater than the maximum test epoch or, that there has been recent exposure to intense sound pressure level, then another test is administered in a step 566. The resulting test metrics are stored in steps 568, 570. In a step 571, the newly determined test metrics are compared to the initial test metrics to calculate any change in the metrics. In step 572, it is determined whether the change is predictive of hearing damage. If not, then in a step 582, the tau is modified according the obtained metric.

If it is determined that hearing damage is predicted, then in a step 578 the user is recommended to remove themselves from the noise as discussed above with the operation of listening fatigue calculator 130 and furthermore, the user can be recommended to seek professional audiological evaluation in a step 578. This could be done by an in situ auditory or visual warning in step 580 by system 100. On the other hand, if system 100 is used in connection with a communications device such as a telephone or a personal digital assistant, an e-mail can be created in steps 574, 576; not only warning the user of potential damage, but notifying a health professional so that a follow up examination can be performed.

It should be noted that a change in the hearing metric (e.g., a hearing sensitivity curve) is measured by system 100. In response to the user's hearing metric, the recovery time constant tau is updated. For example, tau is lengthened if the change in the user's hearing metric indicates the user has "sensitive ears", i.e., if, following intense sound exposure, the user's hearing sensitivity takes longer than the exponential function with time-constant of seven hours to return to the individual's normal. This modified tau can be used to calculate the sound pressure level dose, in particular in a restorative phase, to determine a better overall effect of sound pressure level exposure.

By providing a monitoring and protective system that is adaptable to existing earpieces and in at least one mode, continuously monitors sound pressure level at the ear until a potentially harmful exposure has occurred, rather than only monitoring for a predetermined time as with Noise Dose monitors which monitor for work shifts, a more accurate predictor of harm to the ear is provided. By utilizing a method, which determines exposure in part as a function of effective quiet exposure as well as intense noise exposure, an enhanced model of potential risk is achieved. By providing a series of warning mechanisms and preventive measures as a function of the determined potentially harmful dosage levels ear damage is more likely to be prevented. By providing the system in an earpiece which substantially occludes the ear and making use of audio inputs (if available) at the lateral and medial portions of the ear canal (particularly with an occluding device between lateral and medial portions of the ear canal), a more accurate reading of noise level is provided and more control through a real time warning system is achievable.

It should be known that values for level change threshold, effective quiet time, and epoch were used above as examples. However, it should be noted that any values which when input and utilized in accordance with the methodologies above prevent permanent damage to the ear are within the scope of the invention and the invention should not be so limited to the specific examples above.

Further Exemplary Embodiments

FIG. 8 illustrates the general configuration and some terminology in accordance with descriptions of exemplary embodiments. An earpiece 800 can be inserted into an ear canal separating the ambient environment (AE) 890 from an inner ear canal (IEC) 880 region, where a portion of the earpiece 800 touches a part of the ear canal wall (ECW) 870. The earpiece 800 can be designed to vary its distance from the ear drum (ED) 860. The earpiece 800 can have various elements, and the non-limiting example illustrated in FIG. 8, can include one or more sound producing or receiving elements coupled to input/output 840. In the illustration, an ambient sound microphone (ASM) 830 is configured to sample the AE 890; an ear canal microphone (ECM) 820 is configured to sample the IEC 880; and an ear canal receiver (ECR) 810 is configured to acoustically emit into the IEC 880.

FIGS. 9A-9C illustrates an example of a temporal acoustic signal and its conversion into a spectral acoustic signature. FIG. 9A illustrates a temporal acoustic signal (AS) 900 on a generic X-Y coordinate system (e.g., Y can be amplitude in dB, and X can be time in sec). A section 910 of the AS 900 can be selected for further processing (e.g., for applying filtering treatments such as a FFT). For the non-limiting example of using a Fast Fourier Transform (FFT) on section 910, a window 920 can be applied to the section 910 to zero the ends of the data, creating a windowed acoustic signal (WAS) 930. An FFT can then be applied 940 to the WAS 930 to generate a spectral acoustic signal (SAS) 950, which is illustrated in FIG. 9C, where the Y-axis is a parameter (e.g., normalized power) and the X-axis is frequency (e.g., in Hz).

FIG. 10 illustrates a generalized version of an earpiece 800 and some associated parts (e.g., ASM 830, ECM 820, and ECR 810) in an ear canal. When inserted the earpiece 800 generally defines the two regions 890 and 880. Through the earpiece 800 there is some attenuation. For example, an ambient acoustic signal (AAS) 1010A, will travel through the earpiece 800 and/or via bone conduction (not shown) and be attenuated forming an attenuated ambient acoustic signal (AAAS) 1010B. The AAAS 1010B then travels to the eardrum (ED) 860. The other additional acoustic signal 1010C (e.g., the ECR generated AS or ECRAS), which can travel to the eardrum 860, can be generated by the ECR 810. Thus the total AS imparting energy upon the ED 860 can be due to the AAAS 1010B (which can include a bone conduction part not in the IEC 880) and the ECRAS 1010C. Various exemplary embodiments can calculate SPL Dose due to the total imparting AS upon the ED 860, using various combinations of elements such as the ECR 810, the ECM 820, and the ASM 830. Note that ECM 820 can also measure head attenuated acoustic signals (HAAS) 1010D, which for example could originate from voice.

During operation, a personal audio device outputs a driving signal to ECR 810 so that ECR 810 outputs an acoustic signal 1010C. Similarly, ASM 830 converts the ambient environment noise into an environmental noise signal, which is input to ECR 810 to generate an ECR ambient sound acoustic signal, which could make up a part of acoustic signal 1010C. ECM 820 receives an ambient acoustic signal AAS1010B and the ECR-generated signal 1010C and converts it into a total acoustic sound signal to be operated on by earpiece 800 as discussed below.

FIG. 11 illustrates an earpiece 1100 according to at least one exemplary embodiment comprising an ECR 810. Earpiece 1100 typically couples to one or more sound sources 842 such as a media player, cell phone, or other device that outputs an audio signal. System 100 is a hearing protection module that is coupled to one or more sound sources 842 and the earpiece 1100. System 100 can be connected to a sound source 842 and earpiece 1100 via wired, wireless, fiber optic, and magnetic connections. System 100 can also be housed within earpiece 1100. A sound source 842 is coupled to either analog inputs 11 and 23 or digital input 19. Additional analog or digital inputs can be added if required. Furthermore, it is contemplated that signals can be mixed together to manage, measure, and modify signals. ECR 810 couples to D/A converter 136 such that DSP 134 can provide modified audio content output from earpiece 1100.

ECRAS 1010C can be determined by system 100 through sensing the signal being provided to ECR 810, relating the signal magnitude to a sound pressure level over a period of time, and calculating an equivalent SPL Dose for that period of time. The relationship between signal magnitude and sound pressure level generated by ECR 810 is calculated from data in memory 127 of system 100. The data or relationship can be generated directly from earpiece 1100 and stored in memory 127 during an earpiece modeling process that will be discussed in more detail hereinbelow. Alternately, equations or data can be stored in memory 127 corresponding to different earpiece models. The user can select the appropriate earpiece model stored in memory 127 (or uses a default model) and the equation or data relating to the particular model is used in the calculation of SPL Dose.

Figure 15:
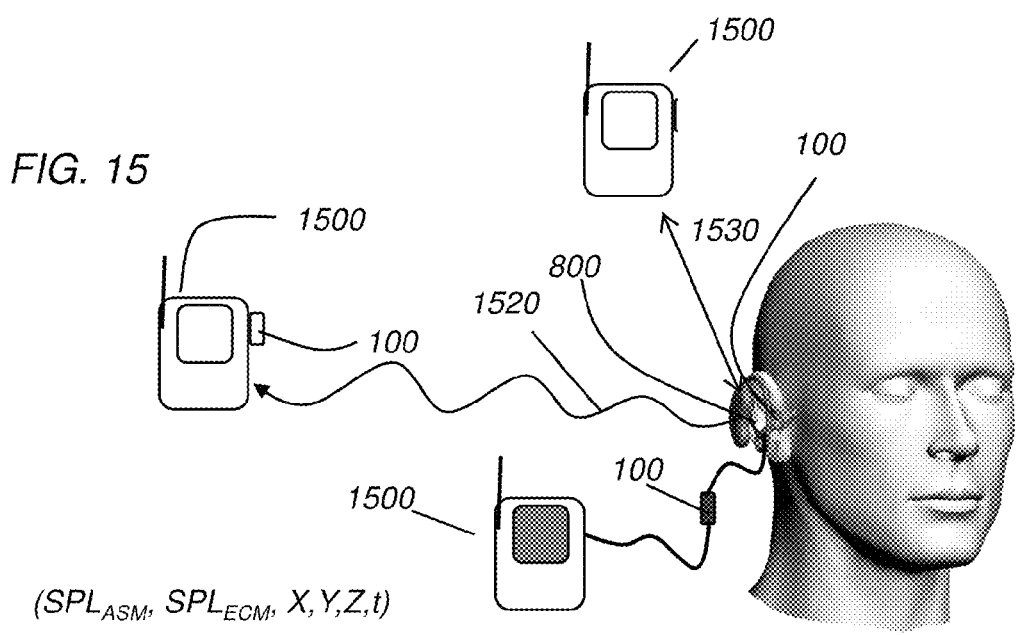
FIG. 15 is an illustration of the system in accordance with at least one exemplary embodiment.

A microphone 844 is operatively coupled to DSP 134 and has an output coupled to either an analog or digital input of system 100. Microphone 844 can be used to measure ambient sound in proximity to the user of earpiece 1100. Referring to FIG. 15, system 100 including microphone 844 is shown attached to a device that outputs an audio signal or attached to an earpiece. In either example, microphone 844 can measure ambient sound near the user of earpiece 1100. Referring back to FIG. 11, the sound pressure level of the ambient sound can be used by system 100 to estimate how much of the ambient sound reaches ear canal 880, which is a combination of AAAS (attenuated ambient acoustic signal) 1010B and HAAS (head attenuated acoustic signal) 1010D. The estimated ambient sound in ear canal 880 is used in calculating the SPL Dose. A warning or action can be taken by system 100 to notify the user of accumulated SPL Dose that can harm the ear or modify the audio content to mitigate damage due to short term or long term exposure to sound.

In general, earpiece 1100 and the earpieces described below periodically measure sound pressure levels of the ambient environment. In at least one exemplary embodiment, the earpieces are used in the work place for hearing protection and also for taking sound pressure level measurements in the work environment to monitor compliance to noise regulations and to identify/correct potential noise issues. Earpiece 1100 and the earpieces described store the SPL measurements in memory 127. SPL_Dose and total SPL_Dose is also stored in memory 127. The measurement of the total SPL_Dose can include a recovery function to improve the accuracy of the time and time period of the measurement is identified by DSP 134. The location of the measurement is identified by GPS 52 or a location detection system. Thus, the SPL, SPL_Dose, total SPL_Dose, time, and location is stored in memory 127 for future analysis. System 100 will provide warning to the user or take preventative action if the SPL_Dose or total SPL_Dose indicates a hazardous condition that could result in hearing damage.

Figure 12:
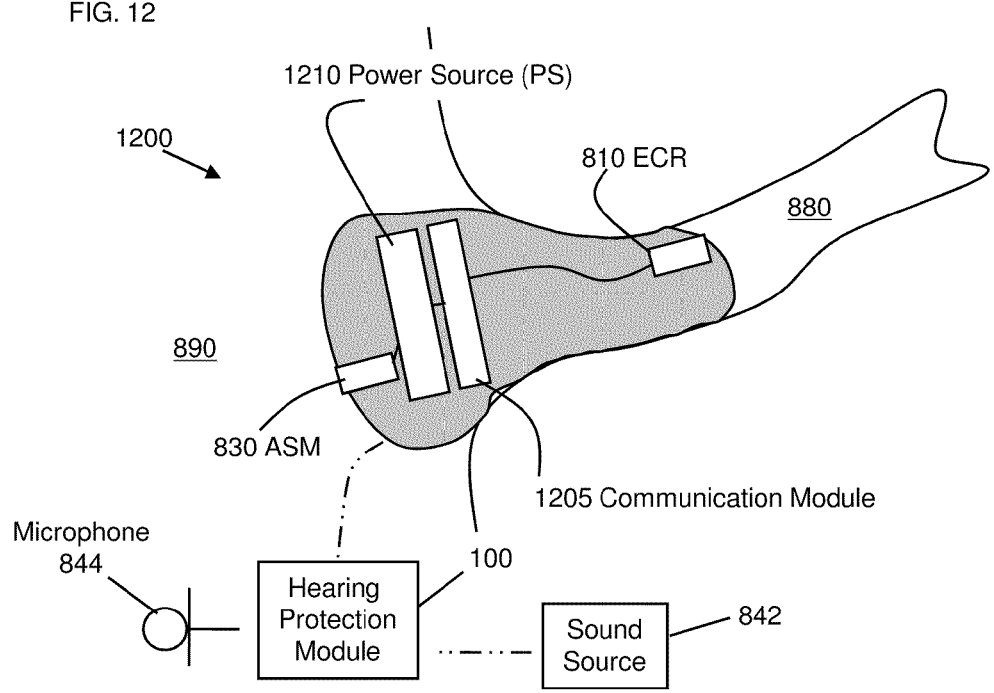
FIG. 12 illustrates an earpiece according to at least one exemplary embodiment that includes an ECR, an ASM, a communication module and a power source.

FIG. 12 illustrates an earpiece 1200 according to at least one exemplary embodiment that includes ECR 810, an ASM 830, a communication module 1205 and a power source (PS) 1210. Communication module 51 of system 100 operatively couples to ECR 810 and ASM 830 through communication module 1205 of earpiece 1200. System 100 receives an audio signal from sound source 842 through a wired or wireless connection. As disclosed above, system 100 can couple to one or more sound sources 842 such as a media player, cell phone, or other device that outputs an audio signal.

ECRAS 1010C is determined by system 100 by sensing the signal being provided to ECR 810 as disclosed above. In at least one exemplary embodiment, system 100 can automatically detect the model of earpiece 1200 and retrieve the appropriate information. The data or equation is then used in conjunction with the measured signal for a calculation of SPL Dose.

The microphone 844 on system 100 is not used in the calculation of SPL Dose because earpiece 1200 has ASM 830. ASM 830 provides an ambient acoustic signal 1010A to system 100. System 100 relates the AAS 1010A measured by ASM 830 to a sound pressure level corresponding to the ambient sound pressure level over the sample period time. Similar to ECR 810, the relationship between signal magnitude and sound pressure level generated by ASM 830 is calculated from data in memory 127 of system 100. The data or relationship can be generated directly from earpiece 1200 and stored in memory 127 during an earpiece modeling process. Alternately, equations or data can be stored in memory 127 corresponding to different earpiece models. The user can select or automatically detect the appropriate earpiece model stored in memory 127 (or uses a default model) and the equation or data relating to the particular model (ASM and ECR) is used in the calculation of SPL Dose.

The sound pressure level due to ambient sound in ear canal 880 is calculated using the measured ambient sound pressure level, attenuation properties of earpiece 1200, and data on the transmission of ambient sound to the ear canal through bone conduction. The ambient sound pressure level in the ear canal is calculated as a combination of AAAS (attenuated ambient acoustic signal) 1010B (earpiece attenuation) and HAAS (head attenuated acoustic signal) 1010D (bone conduction). The estimated ambient sound in ear canal 880 is used in the calculation of the SPL Dose. A warning or action can be taken by system 100 to notify the user of accumulated SPL Dose that can harm the ear or modify the audio content to mitigate damage due to short term or long term exposure to sound.

Figure 13:
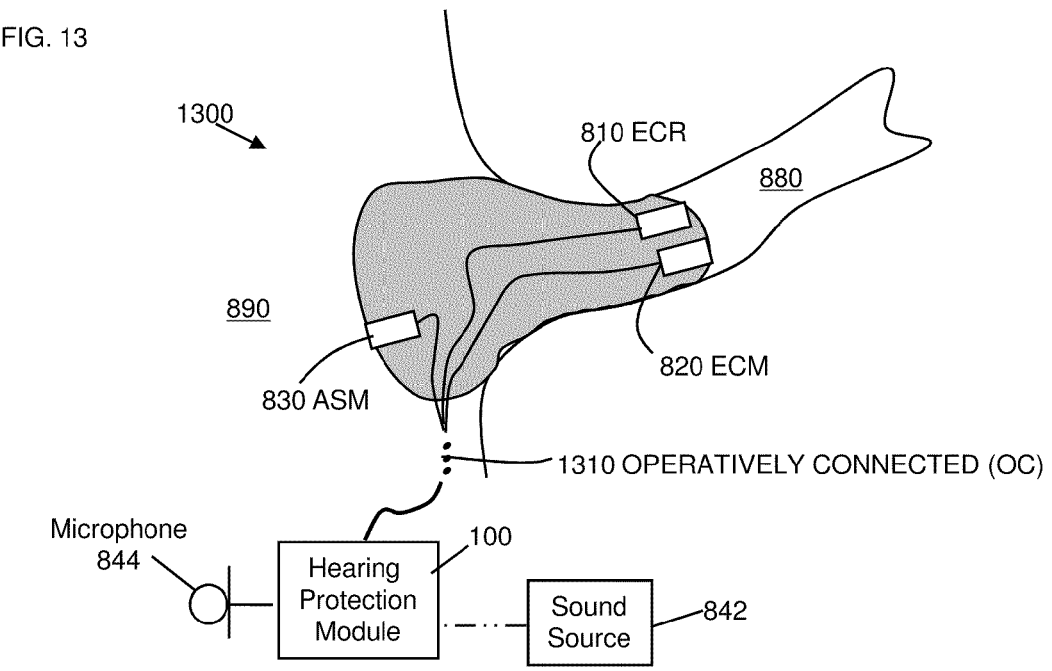
FIG. 13 illustrates an earpiece where some parts are not contained in the earpiece directly, and where optionally an ECM can be used instead of or with an ASM, in accordance to at least one exemplary embodiment.

FIG. 13 illustrates an earpiece 1300 where parts are not contained in the earpiece directly according to at least one exemplary embodiment. Earpiece 1300 comprises ECR 810, ECM 820, and ASM 830. In at least one exemplary embodiment, system 100 operatively couples to ECR 810, ECM 820, and ASM 830 through a wired connection 1310. ECM 820 couples to an analog or digital input of system 100. System 100 receives an audio signal from sound source 842 through a wired or wireless connection.

Note that ECR 810 can also be a dual purpose ECR/ECM, where the function of the transducer can be switched between use as a receiver (ECR 810) and a microphone (ECM 820). In general, ECM 820 is used to measure the sound pressure level in ear canal 880. ECM 820 being located in ear canal 880 can measure in combination AAAS 1010B, ECRAS 1010C, and HAAS 1010D. System 100 relates the magnitude of the signal from ECM 820 to a sound pressure level corresponding to the SPL_Dose over the sample time period. The measured SPL_Dose is used to calculate the new total SPL_Dose. Similarly, ASM 830 is used to measure the sound pressure level in the ambient environment. The relationship between signal magnitude and sound pressure level generated by ECM 820 and ASM 830 is calculated from data about the transducer in memory 127 of system 100. The data or relationship can be generated directly from earpiece 1200 and stored in memory 127 during an earpiece modeling process. Alternately, equations or data can be stored in memory 127 corresponding to different earpiece models.

Figure 14:
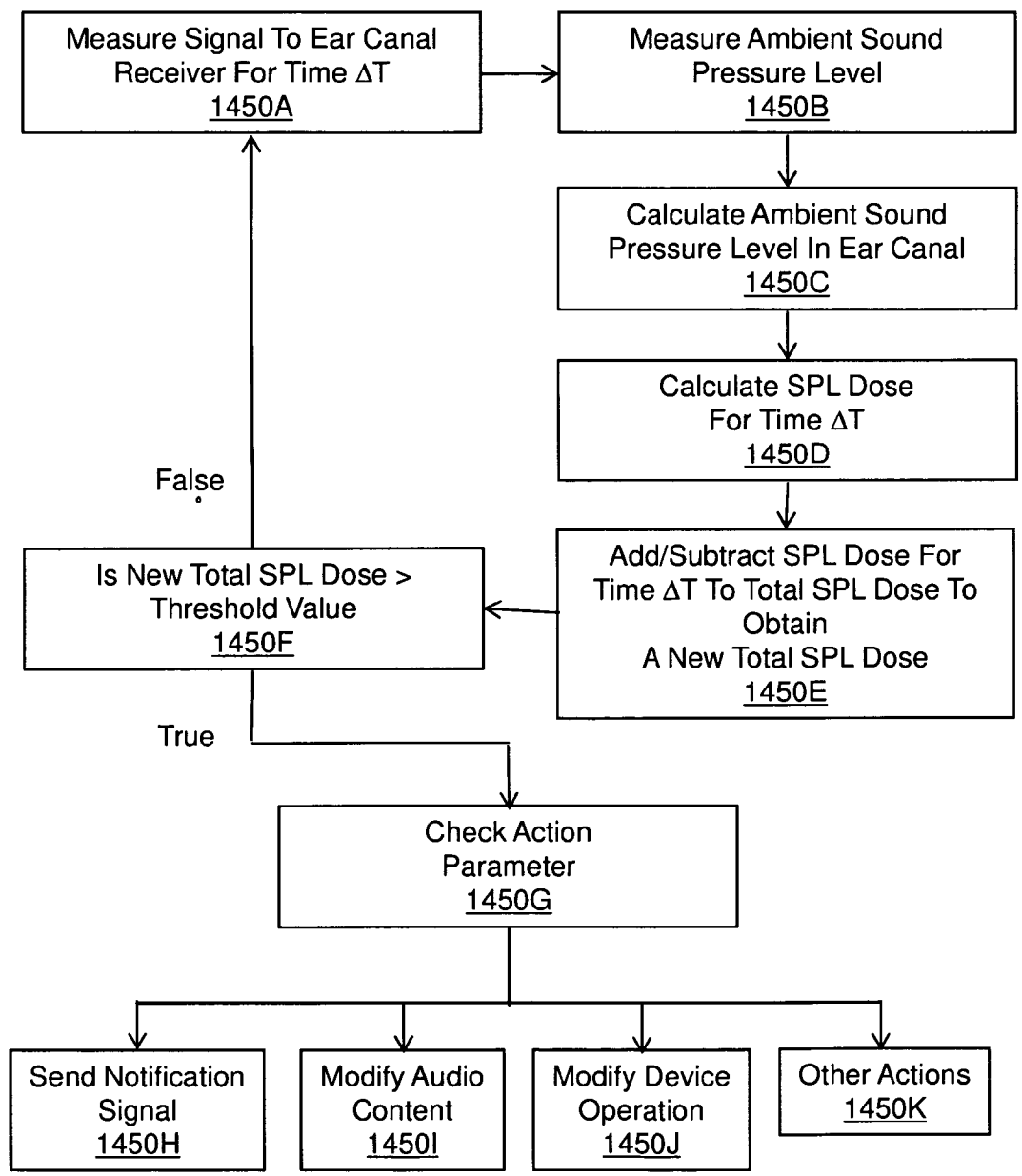
FIG. 14 illustrates a flow diagram of a method for SPL_Dose calculation and response in accordance with at least one exemplary embodiment.

FIG. 14 illustrates a flow diagram of a method for SPL_Dose calculation and response in accordance with an exemplary embodiment. The diagram illustrates the measurements of an earpiece having an ear canal receiver that is coupled to an external system 100 similar to earpiece 41 of FIG. 2A. System 100 resides in a protective housing that couples to the earpiece. This is a non-limiting example, other embodiments of the earpiece are contemplated using different combinations of an ear canal receiver, an ambient sound microphone, ear canal microphone, external microphone, system 100 in the earpiece and system 100 external to the earpiece.

Ambient sound pressure levels are measured by external microphone 844 in proximity to the user. DSP 134 and the other elements of system 100 are powered by a power source such as a battery or power supply. DSP 134 measures audio signals being provided to ECR 810 for output to the user's ear. The magnitude of the audio signal being provided to ECR 810 corresponds to a sound pressure level. As previously mentioned, DSP 134 has stored in memory data, information, or equations for the transducers of the earpiece to calculate or estimate sound pressure levels. DSP 134 can make use of controls, weighting curves, and stored values as discussed above, in order to process the acoustic signals.

Total SPL_Dose is a function of both ambient noise and any driving signals delivered to ECR 810 such as a connected personal audio device, cell phone, or music player. Therefore, in accordance with the invention, in a first step 1450A, the signal being provided to ECR 810 is measured for a time period $\Delta T$ and a sound pressure level is calculated from the signal.

In at least one exemplary embodiment, the ambient noise reaching the user's eardrum is calculated and added to the SPL_Dose. In a step 1450B, the ambient sound pressure level is measured. The ambient sound pressure level is measured by the external microphone of system 100 for the time period $\Delta T$ and the signal provided to DSP 134. DSP 134 calculates the ambient sound pressure level for the time period $\Delta T$ from the external microphone signal.

The measured ambient sound pressure level represents the sound outside the ear and not in the ear canal of the user. In a step 1450C, DSP 134 calculates the ambient sound pressure level in the ear canal. DSP 134 uses the measured ambient sound pressure level and calculates AAAS 1010B, which is the attenuated ambient acoustic signal. In at least one exemplary embodiment, DSP 134 uses a representative attenuation value or equation for the attenuation provided by the earpiece. For example, an equation representative of the attenuation of the earpiece over a predetermined frequency range (e.g. human hearing range) could be used in conjunction with the frequency components and sound pressure levels of the ambient sound measured during the time period $\Delta T$ to provide an accurate calculation of AAAS 1010B. Similarly, DSP 134 calculates HAAS 1010D, which is the head attenuated acoustic signal. A portion of the ambient noise is conducted through the head, which can be represented by a constant attenuation value or in a more sophisticated frequency/SPL dependent equation. The calculated AAAS 1010B and HAAS 1010D can be combined to represent a sound pressure level value present in proximity to the eardrum of the user during the time period $\Delta T$.

In a step 1450D, an SPL_Dose equivalent is calculated for the time period $\Delta t$ in accordance with any of the exemplary methods discussed herein. In general, the calculated sound pressure level provided by the ear canal receiver is combined with the calculated AAAS 1010B and HAAS 1010D to represent the SPL_Dose for the time period $\Delta T$ that the user ear has been subjected too.

In a step 1450E, the calculated SPL_Dose for the time period $\Delta T$ is added to, or subtracted from, the current Total SPL_Dose to obtain a new Total SPL_Dose. In this way the total is continuously updated and monitored. It is understood that if the SPL_Dose for the time period is a restorative dose, then the effect during the time period $\Delta t$ is negative relative to damage and therefore is subtracted from the Total SPL_Dose at time t to obtain the new Total SPL_Dose. Conversely, if the calculated exposure during the time period is greater than a permissible sound level (PSL), the SPL_Dose for the current time period $\Delta t$ is considered potentially damaging and will be added to Total SPL_Dose.

In a step 1450F, it is determined whether or not the Total SPL_Dose is greater than a threshold value. If the Total SPL_Dose has not increased to more than a threshold value, then the process is repeated in step 1450A. If the Total SPL_Dose is greater than the threshold value then DSP 134 checks for action parameters to be taken in a step 1450G. An action parameter corresponds to the corrective action to be taken.

In a step 1450H, the action parameter could correspond to sending a notification signal such as an audio signal, output by the ear canal receiver or a visual notification on the associated personal audio device. Alternatively, the action parameter could correspond to modifying the audio content through attenuation in a step 1450I as discussed above. Furthermore, the action parameter could correspond to modifying the operation of the personal audio device itself in a step 1450J in which the device either shuts off or attenuates its output signal at its origination rather than attenuating the output signal at the ear canal receiver as in step 1450I. Other actions may be taken like those suggested above or others in a step 1450K.

As mentioned previously, it is well within the scope of the invention to modify the described method depending on which transducers are present. For example, if ear canal microphone 820 is included in the earpiece the SPL_Dose and total SPL_Dose can be calculated directly off of measurements in the ear canal instead of using ambient sound measurements. Additionally, if ear canal microphone 820 is present in the earpiece it can be utilized to detect the user's own voice as it is perceived within inner ear canal 880. DSP 134 distinguishes between the user's own voice and the voices of others by determining a difference in the relative intensity of the voices measured by the ear canal microphone. Intensity is a function of the measured SPL_Dose. Therefore, by calculating relative SPL_Dose using the ear canal microphone, DSP 134 can differentiate between and account for the voice of the user.

In one non-limiting example, the ear canal microphone measures acoustic signals below a certain threshold such as 40-50 dB. This is most likely, in one embodiment, lower than the received speaking voice SPL of the user of earpiece at the ear canal. Therefore, DSP 134 determines that voice frequencies at SPL levels below this threshold are not the speaking voice of the user. Of course, the predetermined threshold level can be tuned from user to user depending upon their range of speaking voice from whisper to shout.

In another embodiment, ASM 830 can also measure the voice of the user as a part of ambient environment 890 and compare that value to the SPL of the voice of the user as measured in the inner ear at ECM 820. The SPL_Dose measured attributable to the user's voice within the inner ear should be greater than the value of the voice as part of the ambient environment 890. Therefore, DSP 134 determines whether the ECM SPL_Dose is greater than the ASM SPL_Dose to determine whether or not words received belong to the user or a third party.

An Example of Calculating SPL

SPL exposure within the ear canal in accordance with the invention is a function of noise from both the ambient environment and generated within the ear canal by ECR 810 as a function of input signals thereto. An accurate way to measure SPL exposure is to actually measure the noise level in inner ear canal 880 using ECM 820 if present on the earpiece using system 100. As disclosed hereinabove, the noise level can be measured by monitoring the signal to ECR 810, measuring the ambient sound level, and calculating the ambient sound level in the inner ear canal 880. For the purpose of preventing hearing damage and the method disclosed below the processes are similar resulting in system 100 providing a response or action when the user's ear can be harmed through excessive sound exposure. Accordingly estimated SPL_Dose may be calculated in one embodiment as follows:

$$\text{SPL\_Dose}_{ECM+ASM} = \text{SPL\_Dose}_{ECM+ASM-1} + \text{Time of Sound Exposure/Time } 100\% \quad (15)$$

where Time 100%=24 hrs/$2^{((L_{ECM+ASM}-80)/3)}$
where $L_{ECM+ASM}$ is the measured Ear Canal dBA SPL by the ECM 820 and the ambient SPL by the ASM 830. It is anticipated that the purpose of the ASM 830 will be to allow pick-up of environmental sound, but not necessarily contribute to the determination of SPL_Dose in this embodiment. For example equation (15) can be dependent only upon the ECM value measured. Hence, $L_{ECM+ASM}$ may be analogous to $L_{ECM}$ alone. So $ASM_{-1}$ and ASM go to zero over time and only the ECM component need be accounted for. Thus, the SPL_Dose can contain only measured components from the ECM 820. If for some reason the ECM 820 cannot be used, a backup value of SPL measured by ASM 830 corrected for an NRR of the earpiece added to estimate SPL emitted by the ECR 810 can be used as a less accurate value of using the SPL value measured by the ECM 820. The Time of Sound Exposure is the time during which $L_{ECM+ASM}$ occurs.

The value of 80 in determining time is a threshold value of interest for decibels of the sound level in this one exemplary embodiment. As discussed above, 80 does have some significance to audiologists, but the number may also be the effective quiet, or any other level predetermined by a person skilled in the art designing the system as a function of noise exposure a user will be allowed to experience.

In at least one exemplary embodiment one can determine Free Field Equivalent (FFE) dBA SPL for purposes of determining pressure level dose, the ear canal dBA SPL may be converted to FFE dBA SPL using Table 1 of ISO 11904-1 (2002).

FIG. 15 is an illustration of system 100 in accordance with an exemplary embodiment. In one exemplary embodiment, system 100 includes a housing that can be attached in proximity to the user/earpiece for mitigating hearing damage and measuring sound pressure levels. In another exemplary embodiment, system 100 is integrated into the earpiece. Three variations of system 100 coupled to a device 1500 and earpiece 800 is shown. The coupling is by wired or wireless connections. In a first exemplary embodiment, system 100 has a fold out connector from the housing of system 1000 that is compatible with common electronic devices that output an audio signal such as a cell phone, PDA, multimedia device, or audio player. The connector or jack fits into the device 1500 for receiving an audio signal. The jack also physically holds system 100 onto device 1500. System 100 can be in wired or wireless communication with earpiece 800 for monitoring sound provided to the ear canal of the user and maintaining a total SPL_Dose to compare with a threshold value.

In a second exemplary embodiment, system 100 can be attached to earpiece 800. This would keep system 100 proximate to the user's ear. In at least one exemplary embodiment, system 100 can be in wired or wireless communication 1520 with the transducers of earpiece 800 for monitoring signals and modifying audio content provided to the user. In at least one exemplary embodiment, system 100 includes a global positioning circuit 52 for providing an X, Y, and Z coordinates for the user position.

In a third exemplary embodiment, system 100 is in a housing of earpiece 800. System 100 is connected to transducers of earpiece 800. System 100 can be in wired or wireless communication 1530 with device 1500. System 100 monitors signals from device 1500 and can modify audio content to mitigate hearing damage as disclosed hereinabove. System 100 uses transducers of earpiece 800 to measure sound pressure levels, SPL_Dose, and total SPL_Dose while the user is wearing the device. System 100 can also provide time and position of each measurement and stores the information in memory.

Figure 16:
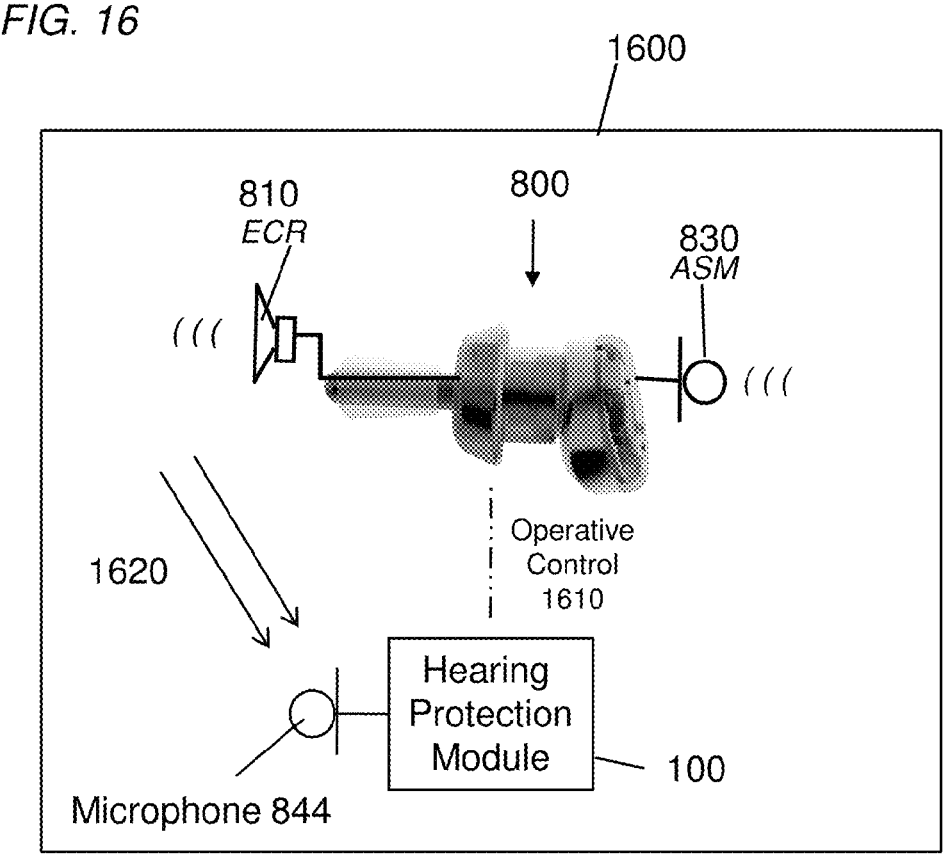
FIG. 16 is an illustration of a modeling process in accordance with at least one exemplary embodiment.

FIG. 16 is an illustration of a modeling process in accordance with an exemplary embodiment. Although a single earpiece is discussed herein the method disclosed for modeling a single earpiece applies similarly to a second earpiece. System 100 generates data or models the specific earpiece 800 used by the user to accurately measure sound pressure levels. System 100 has a microphone 844 having known characteristics for measuring audio acoustic signals/sound pressure levels. As shown, earpiece 800 includes ECR 810 and ASM 830. System 100 is operatively coupled to earpiece 800 and more specifically has operative control 1610 of ECR 810 and ASM 830. In at least one exemplary embodiment, microphone 844 is acoustically coupled to ECR 810 such that sound output by ECR 810 is received without interference from other noise sources to generate data or a model. For example, a tube of known length is fitted to the acoustic stent of earpiece 100 and microphone 844 that acoustically couples sound from ECR 810 to microphone 844. In another embodiment, the housing of system 100 has a receptacle for receiving an earpiece. The receptacle has an opening that couples to microphone 844. The user presses earpiece 800 into the receptacle thereby acoustically coupling microphone 844 to ECR 810. In at least one exemplary embodiment, the receptacle is flexibly shaped similar to an ear concha and ear canal for receiving earpiece 800. The receptacle also physically holds earpiece 800 in place. Alternately, an enclosure 1600 provides a closed environment for acoustically coupling microphone 844 to ECR 810. Enclosure 1600 can be designed to hold system 100 and earpiece 800 for optimal acoustic coupling.

System 100 provides a sequence of electrical signals to ECR 810. ECR 810 generates acoustic signals 1620 corresponding to the electrical signals that are received by microphone 844. The electric signals provided by system 100 determine the relationship of signal frequency/magnitude to sound pressure level generated by ECR 810. System 100 creates a look up table for the data or a model that is stored in memory for use in calculating sound pressure levels output by ECR 810 when the user uses earpiece 800.

Once ECR 810 is modeled it can be used to model or collect data on ASM 830. Modeling ASM 830 (or using known model/data provided by the manufacturer on the transducer) allows the microphone 844 to be used for ambient sound pressure level measurements. Alternately, microphone 844 can be used for the ambient sound pressure level measurements if information on ASM 830 is unknown or cannot be modeled. It is desirable to use ASM 830 because it will be in closest proximity to the ear of the user.

ECR 810 is acoustically coupled to ASM 830. In a first embodiment, an acoustic channel is provided that couples the ports of ECR 810 and ASM 830 together. For example, a flexible tube having a first and second end that respectively fits into the acoustic port of ECR 810 and acoustic port 830. In a second embodiment, enclosure 1600 can also be used to house both system 100 and earpiece 800 to acoustically couple the transducers together. System 100 provides an electric signal to ECR 810 to output an acoustic signal (corresponding to known sound pressure levels) that is received by ASM 830. System 100 provides different frequencies and magnitudes to ECR 810. The known sound pressure levels provided by system 100 determine the relationship to the signal frequency/magnitude output by ASM 830. System 100 creates a look up table for the data or a model that is stored in memory for use in calculating sound pressure levels measured by ASM 830.

Another approach is to provide equivalent sound pressure levels to microphone 844 and to ASM 830. Since the sound pressure level can be measured with microphone 844 it can then be correlated to the signal response of ASM 830. In the descriptions above, system 100 is provided information to compensate for losses in the acoustic coupling methodologies between transducers that could modify the results, model, or data generated.

Figure 17:
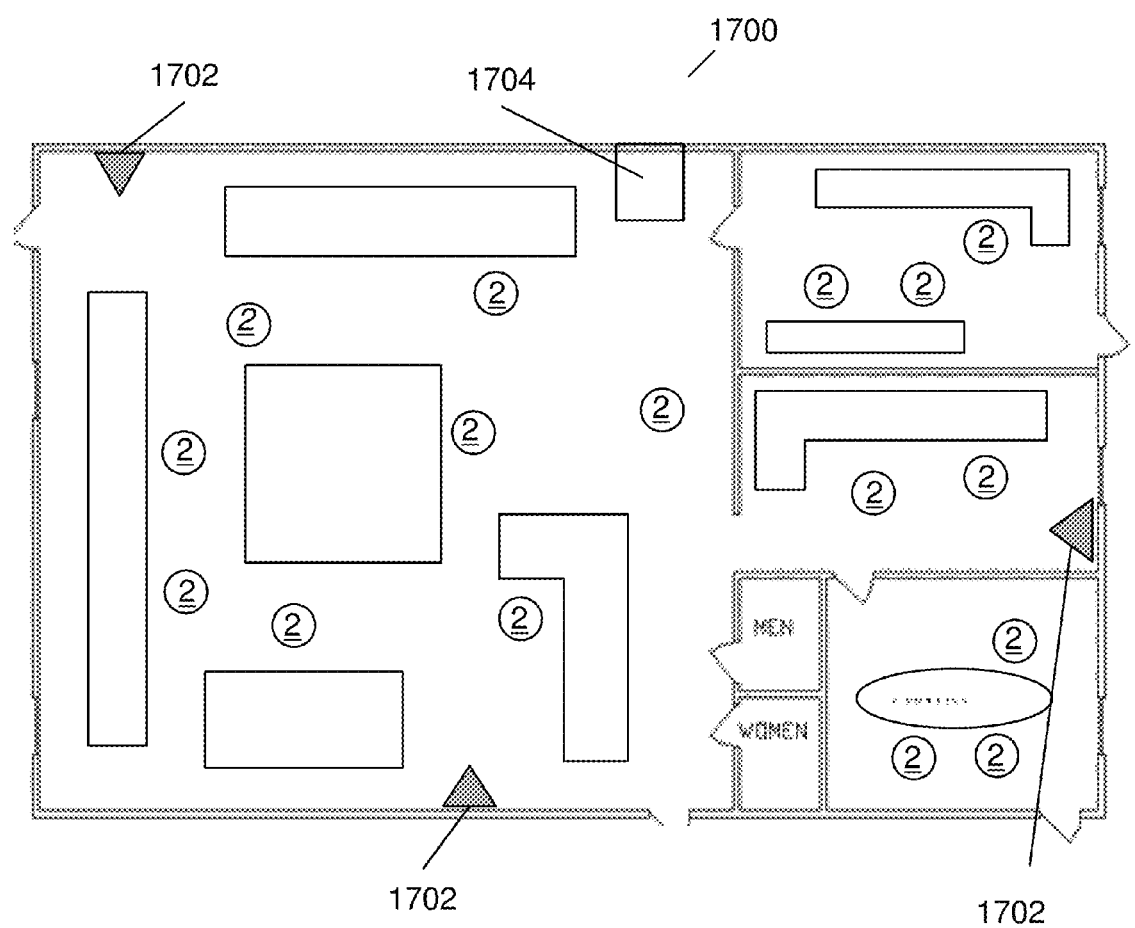
FIG. 17 is an illustration of a floor of a work environment in accordance with at least one exemplary embodiment.

FIG. 17 is an illustration of a floor 1700 in a work environment in accordance with at least one exemplary embodiment. Floor 1700 is a non-limiting example of one floor of a manufacturing environment in a multi-story building that uses machinery that poses a health risk to the hearing of workers 2. Continuously measuring SPL in the building will help owners of the company to monitor noise exposure of their employees, monitor self induced noise exposure, locate areas of high noise level, aid in the deployment of strategies to protect their employees from long term noise induced hearing loss and maintain government compliance to noise standards. In at least one exemplary embodiment, workers are fitted with earpieces described herein for attenuating noise they receive due to manufacturing or other noise sources on floor 1700. The earpieces periodically measure sound pressure levels in the work area.

In at least one exemplary embodiment, the earpieces used by workers 2 include an ultrasonic transmitter that outputs a ping signal for use in conjunction with position detectors 1702. The ping signal can include a unique code related to a specific earpiece. At least three position detectors 1702 are used to determine a location of a particular worker. The ping signal output by an earpiece is detected by position detectors 1702 and a location is determined through triangulation. Placing position detectors 1702 local to the area or volume where the measurement occurs ensures that the position of a sound pressure level measurement can be accurately determined. The position detectors 1702 are in communication with the earpieces to provide location and time information on each measurement taken.

In at least one exemplary embodiment, sound pressure level measurements are taken by earpieces of workers 2 periodically. The position detector system can be used in conjunction with the earpieces to change the period in which measurements are taken. For example, the measurements can be taken more frequently if changes in sound pressure levels are detected. Conversely, the period between measurements can be less frequent if a similar sound pressure level is continuously measured (example measurements stay within ±1 dB). The earpieces prompt position detectors 1702 for position and time information as the measurement is taken. The position detection system sends the information to the earpiece and is attached to the measurement or calculated sound pressure level, SPL_Dose, and total SPL_Dose. The measurement may or may not be used if the person is moving which would be indicated by a significant position change during the measurement (although the position detection system could track the movement of the individual). The sound pressure level measurement is stored in memory of the device. The SPL_Dose can is measured and the total SPL_Dose updated based off of the new measurement.

The earpieces worn by workers 2 generate a volume of data on noise levels and noise exposure in the work environment during the course of a workday. In at least one exemplary embodiment, the sound pressure level measurement, SPL_Dose, total SPL_Dose, time, and location information is stored in memory of system 100 (if located external to the earpiece). Referring to FIG. 20, a charger 2000 is provided for charging an earpiece 2002 after the worker has finished using the device at the end of a workday. The charger 2000 couples wirelessly or through a wire cord for charging and sending information. A communication link 2004 is established between database 1704, charger 2000, and earpiece 2002. In one example, charger 2000 has a tray in which the earpiece is placed for coupling without cables. Charger 2000 is coupled to earpiece 2002 for charging using an electromagnetic field. Earpiece 2002 detects the charging apparatus wirelessly connects to charger 2000 through a Bluetooth or other wireless protocol for providing sound pressure level information. In another exemplary embodiment, a cable is attached to the earpiece from charger 2000 for providing connections to charge the battery and to communicate to system 100. Charger 2000 also has provisions for coupling to system 100 for charging and communication if it is in a separate housing than earpiece 2002.

Alternatively, the earpieces of workers 2 can be in wireless communication with database 1704 while being worn. The measured SPL, SPL_Dose, and total SPL_Dose measurements with the corresponding time and position data is downloaded to database 1704 at intervals during the course of the day. The sound pressure level data can then be analyzed as it is received. In general, the user of earpiece 2002 can receive information on the total_SPL Dose received during the course of the day thereby providing information to aid in mitigating hearing damage when the worker leaves the premises.

Figure 18:
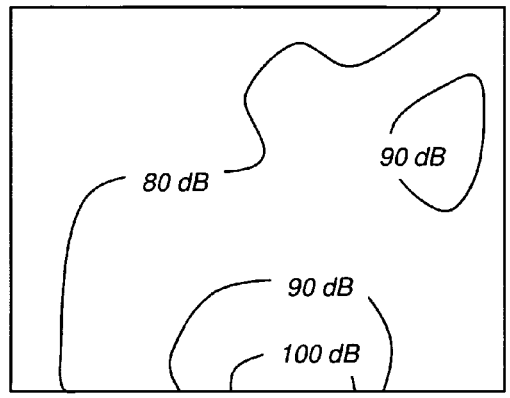
FIG. 18 illustrates a contour map that can be generated from the SPL measurements taken by one or more earpieces in accordance with at least one exemplary embodiment.

FIG. 18 illustrates a contour map 1800 that can be generated from the SPL measurements taken by one or more earpieces in accordance with at least one exemplary embodiment. For example, data from database 1704 is used to create a sound pressure level map of the work environment for a specific time or time period (average SPL). Other maps can be generated at different times to determine how the SPL changes with time or worker operated machinery. A contour line shows regions of approximately equal sound pressure level. Contour lines of 80 dB, 90 dB, and 100 dB are indicated on the map.

Contour map 1800 indicates areas where noise levels could be an issue for workers unless precautions are taken. Once isolated, the company can take steps to reduce the sound exposure of their workers. For example, a particular piece of equipment located where 100 dB sound pressure levels are generated could be placed in a chamber for reducing noise it couples to the ambient. Alternatively, steps could be taken to dampen or reduce the sound produced by the machinery. Contour map 1800 can also show secondary effects that could compound the noise problem. Multiple pieces of equipment in combination with each other could produce exceedingly high sound pressure levels. Contour map 1800 can indicate that moving the noise sources from one another or adjusting the schedule when the equipment is operated can have a significant impact on reducing sound pressure levels.

Figure 19:
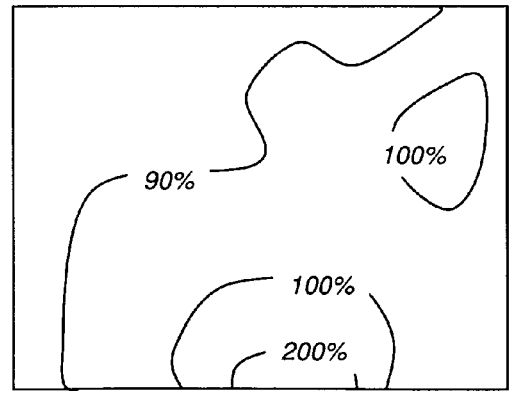
FIG. 19 is an illustration of a contour map that can be generated from SPL_Dose measurements taken by earpieces in accordance with an exemplary embodiment.

FIG. 19 is an illustration of a contour map 1900 that can be generated from SPL_Dose measurements taken by earpieces in accordance with an exemplary embodiment. In at least one exemplary embodiment, the SPL_Dose and total SPL_Dose is measured using an earpiece as described hereinabove. In the example illustrated in FIG. 6 dosage information such as SPL_Dose with recovery function, SPL_Dose without recovery function, and/or noise dose according to various standards (e.g. OSHA) is displayed either for a particular time period or averaged over a time period. For example, a particular time period could be a normal eight-hour workday.

As mentioned hereinabove, measurement data from the earpieces can be stored in a database 1704. The measurement data is used to create a SPL_Dose contour map 1900 of the work environment for a specific time or time period. The SPL_Dose can be an average over the time period, peak SPL, or some other weighted measure of SPL_Dose. Other maps can be generated at different times to determine how the SPL_Dose changes with time or worker operated machinery. A contour line shows regions of approximately equal SPL_Dose as a function of the percent allowable dose. Contour lines of 90%, 100%, and 200% are indicated on the map. The contour of 100% dose would suggest that a person in proximity to this contour line could generate hearing damage if the ears were unprotected. The contour line of 200% would require ear protection to minimize the risk of hearing damage.

Contour map 1900 indicates areas where the SPL_Dose can be an issue for workers hearing health unless precautions are taken. Similar to precautionary measures disclosed above, the company can take steps to reduce the sound exposure of their workers. Contour map 1900 can indicate that moving the noise sources from one another or adjusting the schedule when the equipment is operated can have a significant impact on reducing sound pressure levels. It should be noted that SPL_Dose and total SPL_Dose takes into account sound provided to the ear other than ambient noise. For example, if a worker is listening to music at very loud levels with the earpiece the could generate a high SPL_Dose value when the ambient conditions are benign. This technique of mapping sound pressure levels using earpieces can be used for many applications both indoors and outdoors, on city streets or in parks, in hotels, shopping malls, schools and other areas where loud sounds occur naturally or man made.

FIG. 21 is a graph 2100 of a measurement of sound pressure level 2102 and SPL_Dose 2104 in accordance with an exemplary embodiment. The y-axis of the graph illustrates the sound pressure level in decibels (dB) and the SPL_Dose in percentage. The time is indicated in the x-axis and is shown for the hours 4 pm to 12 pm (8 hours). At the start of the measurement period SPL_Dose 2104 is at the lowest point (approximately 30%). The wearer of the earpiece(s) has substantial margin before exceeding sound safety limits. The sound pressure levels measured by the earpieces for the majority of the time period are at a level greater than line 2106. The user receiving sound pressure levels above line 2106 will increase the SPL_Dose. Conversely, SPLs lower than line 2106 will allow the ear to recover thereby reducing the total SPL_Dose according to a recovery function.

Note that the SPL_Dose increases as the user receives sound pressure levels above line 2106. After 10 pm, the sound pressure levels fall below line 2106 and the SPL_Dose falls as the ear is given time to recover. In this example, the user is not at substantial risk for hearing damage as the SPL_Dose remains under 60% for the entire 8-hour period. The earpiece would warn or take an action to mitigate hearing damage for both a short-term noise event or if the SPL_Dose would continue to rise to a level where ear health is compromised. As discussed hereinabove, the data of graph 2100 is stored in memory of the earpiece including the location information related to each sound pressure level measurements.

Figures 22, 23:
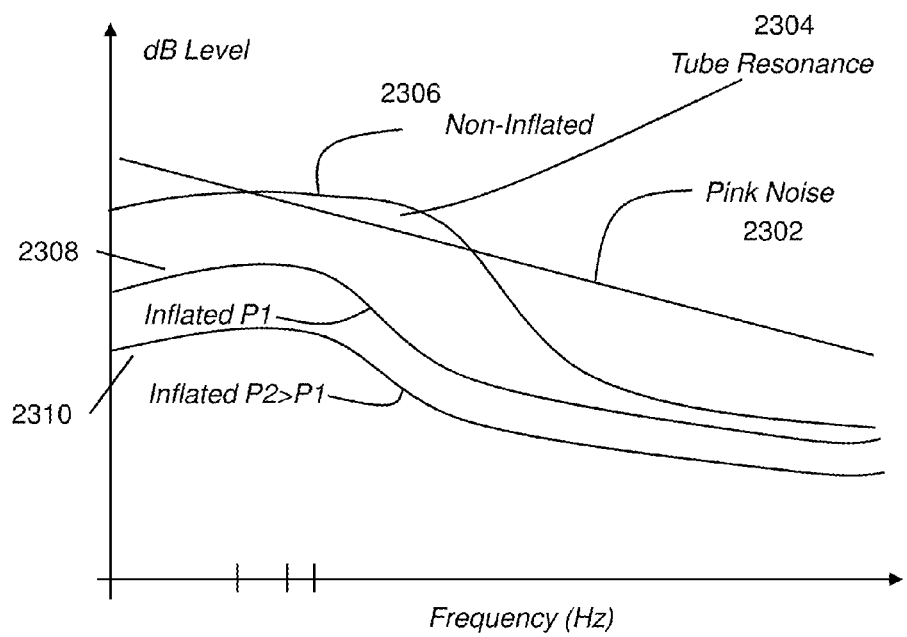
FIG. 22 is a chart indicating memory requirements for storing sound pressure level measurements in accordance with at least one exemplary embodiment.
FIG. 23 is a graph illustrating sound isolation as a function of inflation of an inflatable system in accordance with at least one exemplary embodiment.

FIG. 22 is a chart 2200 indicating memory requirements for storing sound pressure level measurements in accordance with at least one exemplary embodiment. Chart 2200 includes multiple channels for taking measurements. Eight channels are listed although it is likely that less would be used. For example, taking measurements with an ambient sound microphone and a ear canal microphone can use two channels. The measurements have 8 bits of resolution and the memory used for each row is in kilobits of memory. The time period for the measurements is a 24-hour period. The sample frequency in the non-limiting example determines how much memory is required for the 24 hour time period. The first column indicates the sample frequency, 10 samples per second, 0.5 samples per second, and 0.1 samples per second that respectively correspond to taking 600, 30, and 6 sound pressure level measurements per minute. Taking 600 measurements per minute would provide more accuracy if the sound pressure levels varied significantly with time. Conversely, 6 measurements per minute can be accurate if the sound pressure levels are consistent. The measurement rate can be varied over time automatically (as discussed below) or set to a predetermined rate based on knowledge of the environment (dynamic or consistent sound pressure level changes). In either case, chart 2200 indicates that the data can be stored on an earpiece for the 24-hour period. Taking measurements at 10 samples per second would require 6912 kilobits of memory for the 24-hour period (for the SPL measurement data only). Measuring at 0.5 samples per second reduces the memory required to 345.6 kilobits. Additional information such as SPL_Dose, total SPL_Dose, time, and location would increase the amount of memory needed. Data compression techniques could be used to reduce the amount of memory required to store the information.

FIG. 23 is a graph 2300 illustrating sound isolation as a function of inflation of an inflatable system in accordance with at least one exemplary embodiment. The inflatable system is designed to seal an opening of an ear canal. As mentioned hereinabove, two separate regions are formed by the inflatable system. In a first region pink noise 2302 is provided corresponding to a first side of the inflatable system. In a second region (isolated by the inflatable system) measurements are taken to determine the amount of sound isolation provided by the inflatable system. A microphone placed in proximity to the first side of the inflatable system measures the pink noise 2302. A second microphone, placed in the second region measures the amount of isolation achieved by the inflatable system. Additionally, the inflation medium can be either a liquid, gas, gel, or other medium to increase/decrease the pressure within the inflation medium (e.g. balloon) to form a seal that isolates the second region from the first region.

The curve 2306 represents the inflatable system when it is not completely sealed. Even though the sound passes by the inflatable system, the measured signal in the second region varies in level across the frequency band. The portion 2304 of curve 2306 that is above the pink noise signal is due to resonance in the second region. As shown, both the low frequency and high frequencies are attenuated in the second region.

A curve 2308 represents the inflatable system at a first pressure P1 greater than or equal to a seal pressure where the inflatable system has conformed to the inside of the ear canal opening (e.g. whether regular or irregular). At the seal value pressure there will be a drop between the sound pressure level of the first side to the second side of the inflatable system. This is indicated by curve 2308 being less than curve 2302 at all frequencies. In general, the amount of isolation varies over frequency. A curve 2310 represents the inflatable system inflated to a second pressure P2 greater than pressure P1. Increasing the pressure in the inflatable system provides improvement of the attenuation properties of the system.

The principal of increasing and decreasing pressure can be used to enhance protection of an earpiece user. The inflatable system can be kept at the sealing value pressure (or slightly greater) under normal operating conditions to maximize comfort to the user. For example, minimum pressures can be used under moderate noise levels where the measured sound pressure levels and SPL_Dose does not indicate a potential harmful situation to the user. Conversely, the earpiece upon detecting a rise in sound pressure level (e.g. greater than 1 dB) or the average sound pressure level is producing a rise in SPL_Dose then an increase in pressure to the inflatable system can increase attenuation of ambient noise thereby providing further protection. Similarly, detecting benign conditions in the ambient environment, the earpiece could lower the pressure in the inflatable system.

Figure 24:
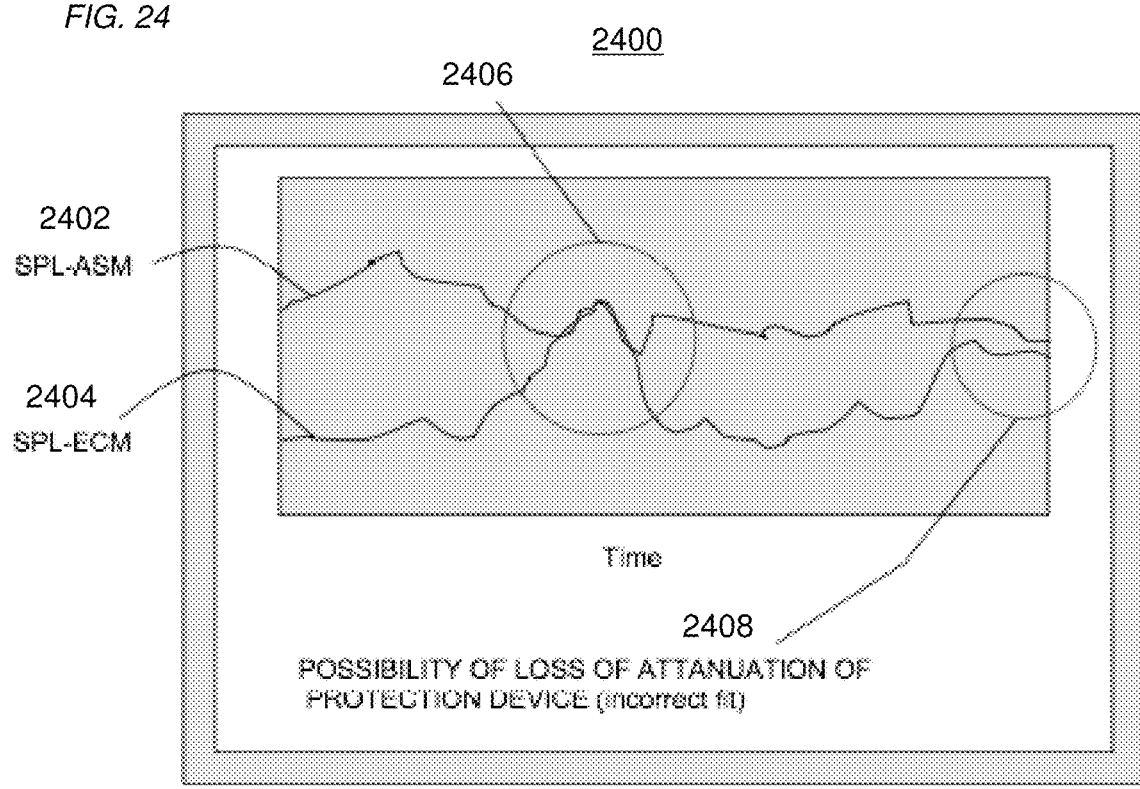
FIG. 24 is a graph indicating an ambient sound microphone and an ear canal microphone measuring similar sound pressure levels in accordance with at least one exemplary embodiment.

FIG. 24 is a graph 2400 indicating an ambient sound microphone and an ear canal microphone measuring similar sound pressure levels in accordance with at least one exemplary embodiment. A curve 2402 is the measured sound pressure level from an ambient sound microphone of an earpiece. A curve 2404 is the measured sound pressure level from an ear canal microphone of the earpiece. Typically, the sound pressure levels should differ by the attenuation capability of the sealing section of the earpiece. At points 2406 and 2408 the measured sound pressure level measured by the ear canal microphone is the same or similar to that measured by the ambient sound microphone. Identifying when the similar ASM and ECM measurements are similar can be used to detect a poor seal in the sealing section or that the earpiece is being removed from the ear. In the event of a poor seal condition, the user could be notified allowing an insertion, reinflation, and sealing test to be performed to ensure the user ear is protected. Detecting removal of the earpiece is beneficial to stopping measurements from being taken that would not be representative of measured SPL_Dose and total SPL_Dose.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, although specific numbers may be quoted in the claims, it is intended that a number close to the one stated is also within the intended scope, i.e., any stated number (e.g., 80 dB) should be interpreted to be "about" the value of the stated number (e.g., about 80 dB). Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method of mitigating hearing damage and providing sound pressure level (SPL) information comprising the steps of:
   attenuating ambient sound from reaching an ear canal of a user by way of an earpiece having at least one transducer including an ear canal receiver (ECR);
   periodically measuring first SPL information in a time period having a plurality of samples from the ambient sound received proximate the earpiece external to the ear canal;
   periodically measuring second SPL information in the time period, synchronous with the first SPL information, from a driving signal provided to the ECR;
   combining, for each time period, the first SPL information and the second SPL information to form combined SPL information;
   storing at least the combined SPL information or an SPL_Dose in a memory with corresponding time and location information over plural time periods;
   using an inflatable sealing section on the earpiece configured to seal an opening to the ear canal of the user to form an acoustic seal to reduce the ambient sound from an ambient environment in a cavity of the ear canal of the user;
   using an ear canal microphone (ECM) configured to measure the sound pressure level in the cavity of the ear canal, to confirm the acoustic seal and to test a hearing sensitivity of the user, wherein a recovery time constant tau used in a recovery function is updated in response to the hearing sensitivity test;
   measuring a total SPL_Dose including the recovery function for indicating an accumulated user sound exposure over an extended period of time that improves an accuracy of the total SPL_Dose measurement over the extended period of time; and
   generating an output by a digital signal processor that adaptively adjusts a sound pressure level of the at least one transducer that accounts for the accumulated user sound exposure over the extended period of time.

2. The method of claim 1 further including the steps of:
   measuring a SPL_Dose from a SPL measurement selected from among at least one of the first SPL information, the second SPL information or the combined SPL information when the SPL measurement is greater than a permissible sound level;
   calculating the SPL_Dose using the recovery function when the SPL measurement is less than the permissible sound level, the recovery function modeling a decrease of the SPL_Dose below the permissible sound level for a measured period of time;
   measuring the total SPL_Dose for indicating the accumulated user sound exposure over the extended period of time that is compared against a threshold value; and
   storing the total SPL_Dose in the memory with the corresponding time and location information.

3. The method of claim 2 further including a step of periodically measuring the SPL_Dose and the total SPL_Dose while the user is wearing the earpiece and storing the SPL_Dose and the total SPL_Dose in the memory with the corresponding time and location information.

4. The method of claim 1 further including adjusting a periodicity of the measuring of the first SPL information and the second SPL information in response to changing sound pressure levels.

5. The method of claim 1 further including the steps of:
connecting the earpiece to a recharging station where the recharging station is wired or wirelessly coupled to a database;
recharging the earpiece;
initiating a connection from the earpiece to the database when the earpiece is connected to the recharging station; and
downloading at least one of the first SPL information, the second SPL information or the combined SPL information from the memory to the database to form stored SPL information.

6. The method of claim 5, wherein the database stores the stored SPL information for a plurality of earpieces, the method further including the steps of:
organizing the stored SPL information by the respective user, a respective location, and a respective time; and
generating at least one map illustrating sound pressure levels in a predetermined area at a predetermined time or over a predetermined time period based on the stored SPL information.

7. The method of claim 1 further including the steps of:
measuring the first SPL information using an ambient sound microphone (ASM) of the earpiece;
measuring third SPL information in the ear canal of the user using the ear canal microphone (ECM) of the earpiece;
comparing the first SPL information of the ASM to the third SPL information of the ECM;
taking an action when the measured first SPL information and the third SPL information are within a predetermined range.

8. A method of using an earpiece in a work environment comprising the steps of:
attenuating sound in the work environment by way of an earpiece including an ear canal microphone (ECM);
periodically measuring sound pressure level information in an ear canal in a time period having a plurality of samples in the work environment using the ECM of the earpiece, where a time and location is included with each measurement;
storing at least the SPL_Dose in a memory over plural time periods;
downloading at least the SPL_Dose over the plural time periods to a database;
analyzing, in the database, at least the SPL_Dose over the plural time periods, to form analyzed information;
identifying potential noise compliance issues in the work environment responsive to the analyzed information;
using an inflatable sealing section on the earpiece to seal an opening to the ear canal of the user to form an acoustic seal; and
using the ear canal microphone to measure the SPL_Dose in the earpiece from the sound pressure level information, to confirm the acoustic seal, to test a hearing sensitivity of a user's ear and for updating a recovery time constant tau used in a recovery function in response to the hearing sensitivity test;
measuring a total SPL_Dose including the recovery function for indicating an accumulated user sound exposure over an extended period of time that accounts for effective quiet levels and improves an accuracy of the total SPL_Dose measurement over the extended period of time; and
generating an output by a digital signal processor that adaptively adjust a sound pressure level of at least one transducer of the earpiece that accounts for the accumulated user sound exposure over the extended period of time.

9. The method of claim 8 further including the steps of:
identifying areas of the work environment having a sound exposure risk based on the analyzed information; and
generating a map of at least one of the sound pressure level information or the SPL_Dose in the work environment at a predetermined time or over a predetermined time interval illustrating the areas of sound exposure risk.

10. The method of claim 8 further including the steps of:
increasing a pressure in a sealing section of the earpiece when the sound pressure level information is greater than a threshold value to increase an attenuation provided by the earpiece; and
decreasing the pressure in the sealing section of the earpiece when the sound pressure level information is less than the threshold value.

11. The method of claim 8 further including the steps of:
measuring a SPL_Dose with the sound pressure level information when the sound pressure level information is greater than a permissible sound level;
calculating the SPL_Dose using the recovery function when the sound pressure level information is less than the permissible sound level, the recovery function modeling a decrease of the SPL_Dose below the permissible sound level;
updating the total SPL_Dose with each sound pressure level information measurement;
storing the total SPL_Dose with each sound pressure level information measurement; and
taking an action to mitigate hearing damage when the total SPL_Dose reaches a maximum allowable total SPL_Dose that accounts for periods of effective quiet levels over a measured period of time.

12. The method of claim 8 further including the steps of:
measuring further sound pressure level information in the work environment using an ambient sound microphone of the earpiece; and
providing sound to the ear canal using an ear canal receiver of the earpiece.

13. The method of claim 12 further including the steps of:
detecting when the sound pressure level information measured by the ear canal microphone is within a predetermined range of the further sound pressure level information measured by the ambient sound microphone; and
responsive to the detecting, initiating an action to the user of the earpiece for determining if the earpiece is correctly sealing the ear canal.

14. The method of claim 8 further including a step of using a microphone in proximity to the earpiece to measure further sound pressure level information in the work environment; and
providing sound to the ear canal using an ear canal receiver of the earpiece.

15. The method of claim 8, wherein the stored sound pressure level information is downloaded to the database when the earpiece is being recharged.

16. A method of mapping comprising the steps of:
attenuating sound by way of a plurality of earpieces where each earpiece includes at least one transducer;
periodically measuring sound pressure levels and a sound pressure level dose (SPL_Dose) in an ambient environment using the plurality of earpieces, where each SPL_Dose is measured using an ear canal microphone of each earpiece when the corresponding sound pressure levels are greater than a permissible sound level, and is calculated using a recovery function when the sound pressure levels are less than the permissible sound level, the recovery function modeling a decrease of the SPL_Dose below the permissible sound level;
storing the SPL_Dose over plural measurements in a database with corresponding time and location information of each measurement;
generating a map of at least the SPL_Dose based on the plural measurements for a predetermined area of the ambient environment over a predetermined time period;
using an inflatable sealing section on the earpiece to seal an opening to the ear canal of the user to form an acoustic seal to reduce the ambient sound from an ambient environment in a cavity of the ear canal of the user; and
using the ear canal microphone configured to measure the sound pressure level in the cavity of the ear canal, to confirm the acoustic seal and to test a hearing sensitivity of the user, wherein a recovery time constant tau used in a recovery function is updated in response to the hearing sensitivity test;
measuring a total SPL_Dose including a recovery function for indicating an accumulated user sound exposure over an extended period of time that accounts for effective quiet levels over the extended period of time; and
generating an output by a digital signals processor that adaptively adjusts a sound pressure level of the at least one transducer that accounts for the accumulated user sound exposure over the extended period of time.

17. The method of claim 16 further including the steps of:
coupling at least one of the earpieces to a recharging system where the recharging system is coupled to the database;
downloading the sound pressure levels to the database when a corresponding earpiece is being recharged;
analyzing the respective sound pressure levels in the database; and
identifying that areas of the ambient environment are in compliance with predetermined noise standards.

18. The method of claim 17 further including the steps of:
increasing a periodicity of the measuring of the sound pressure levels and the SPL_Dose when a change in the measured sound pressure levels is above a SPL difference value; and
decreasing the periodicity of the measuring of the sound pressure levels when the change in the measured sound pressure levels is below the SPL difference value.

19. The method of claim 17 further including a step of increasing a periodicity of the measuring of the sound pressure levels and the SPL_Dose as the sound pressure levels rise.

* * * * *